United States Patent
Territo et al.

(10) Patent No.: US 11,361,407 B2
(45) Date of Patent: Jun. 14, 2022

(54) MOTION CORRECTION SYSTEMS AND METHODS FOR IMPROVING MEDICAL IMAGE DATA

(71) Applicant: Indiana University Research and Technology Corporation, Indianapolis, IN (US)

(72) Inventors: Paul Richard Territo, Fishers, IN (US); Paul Salama, Carmel, IN (US); Juan Antonio Chong, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 16 days.

(21) Appl. No.: 16/603,807

(22) PCT Filed: Apr. 9, 2018

(86) PCT No.: PCT/US2018/026669
§ 371 (c)(1),
(2) Date: Oct. 8, 2019

(87) PCT Pub. No.: WO2018/191145
PCT Pub. Date: Oct. 18, 2018

(65) Prior Publication Data
US 2020/0043143 A1 Feb. 6, 2020

Related U.S. Application Data

(60) Provisional application No. 62/483,434, filed on Apr. 9, 2017.

(51) Int. Cl.
*G06K 9/00* (2022.01)
*G06T 5/00* (2006.01)
(Continued)

(52) U.S. Cl.
CPC ............ *G06T 5/002* (2013.01); *G06T 3/0075* (2013.01); *G06T 7/246* (2017.01); *A61B 5/055* (2013.01);
(Continued)

(58) Field of Classification Search
CPC ...................................................... G06T 5/002
See application file for complete search history.

(56) References Cited

U.S. PATENT DOCUMENTS 6,006,126 A * 12/1999 Cosman ............... G06V 10/245
600/426
2004/0210385 A1 10/2004 Dale
(Continued)

OTHER PUBLICATIONS

Positron Emission Tomography-Computed Tomography (PET/CT), 2017. [Online; Last Date Accessed: Mar. 14, 2017], https://www.radiologyinfo.org/en/info.cfm?pg=pet.
(Continued)

*Primary Examiner* — Oneal R Mistry
(74) *Attorney, Agent, or Firm* — Faegre Drinker Biddle & Reath LLP

(57) ABSTRACT

A computing device is provided having at least one processor (104) operative to facilitate motion correction in a medical image file (102). The at least one processor (104) is configured to generate at least one unified frame file (110) based on motion image data (204), depth map data (206) corresponding to the motion image data, and region of interest data (200). Further, at least one corrected image file derived from the medical image file (102) is generated by performing the motion correction based on the at least one unified frame file (110) using the processor (104). Subsequently, the at least one corrected image file is outputted for display to one or more display devices (122).

15 Claims, 13 Drawing Sheets

(51) Int. Cl.
G06T 7/246 (2017.01)
G06T 3/00 (2006.01)
A61B 5/055 (2006.01)
A61B 6/00 (2006.01)
A61B 8/08 (2006.01)

(52) U.S. Cl.
CPC ............ *A61B 6/527* (2013.01); *A61B 8/5276* (2013.01); *G06T 2207/10104* (2013.01)

(56) References Cited

U.S. PATENT DOCUMENTS

| | | | |
|---|---|---|---|
| 2006/0056698 A1 | 3/2006 | Jolly | |
| 2009/0149741 A1 | 6/2009 | Heigl | |
| 2010/0280365 A1* | 11/2010 | Higgins | A61B 5/418 600/424 |
| 2011/0135206 A1 | 6/2011 | Miura | |
| 2012/0014579 A1* | 1/2012 | Li | A61B 6/032 382/131 |
| 2012/0281897 A1 | 11/2012 | Razifar | |
| 2014/0243671 A1 | 8/2014 | Holl | |
| 2014/0355855 A1 | 12/2014 | Miao | |
| 2015/0139515 A1 | 5/2015 | Smith | |
| 2016/0163031 A1* | 6/2016 | Gordon | G06T 7/536 348/46 |
| 2016/0256127 A1* | 9/2016 | Lee | A61B 6/5264 |
| 2016/0345858 A1* | 12/2016 | Tromberg | A61B 5/1128 |
| 2017/0042511 A1* | 2/2017 | Labyed | A61B 8/5207 |
| 2017/0046833 A1 | 2/2017 | Lurie | |
| 2019/0000564 A1* | 1/2019 | Navab | G06T 7/521 |
| 2021/0073692 A1* | 3/2021 | Saha | G06T 7/0012 |

OTHER PUBLICATIONS

D.C. Owens, E.C. Johnstone, and C. Frith, "Spontaneous involuntary disorders of movement: their prevalence, severity, and distribution in chronic schizophrenics with and without treatment with neuroleptics," Archives of General Psychiatry, vol. 39, No. 4, pp. 452-461, 1982.
J. M. Kane, P. Weinhold, B. Kinon, J. Wegner, and M. Leader, "Prevalence of abnormal involuntary movements (spontaneous dyskinesias) in the normal elderly," Psychopharmacology, vol. 77, No. 2, pp. 105-108, 1982.
R. Menezes, A. Pantelyat, I. Izbudak, and J. Birnbaum, "Movement and other neurodegenerative syndromes in patients with systemic rheumatic diseases: A case series of 8 patients and review of the literature," Medicine, vol. 94, No. 31, 2015.
P.J. Noonan, J. Howard, D. Tout, I. Armstrong, H.A. Williams, T.F. Cootes, W.A. Hallett, and R. Hinz, "Accurate markerless respiratory tracking for gated whole body pet using the microsoft kinect," in Nuclear Science Symposium and Medical Imaging Conference (NSS/MIC), 2012 IEEE. IEEE, 2012, pp. 3973-3974.
X. Jin, T. Mulnix, B. Planeta-Wilson, J.-D. Gallezot, and R.E. Carson, "Accuracy of head motion compensations for the hrrt: Comparison of methods," in 2009 IEEE Nuclear Science Symposium Conference Record (NSS/MIC). IEEE, 2009, pp. 3199-3202.
X. Jin, T. Mulnix, J.-D. Gallezot, and R.E. Carson: Evaluation of motion correction methods in human brain pet imaging a simulation study based on human motion data, Medical physics, vol. 40, No. 10, p. 102503, 2013.
O.V. Olesen, J.M. Sullivan, T. Mulnix, R.R. Paulsen, L. Hojgaard, B. Roed, R.E. Carson, E.D. Morris, and R. Larsen, "List-mode pet motion correction using markerless head tracking: Proof-of-concept with scans of human subject," IEEE transactions on medical imaging, vol. 32, No. 2, pp. 200-209, 2013.
P.J. Noonan, J. Howard, T.F. Cootes, W.A. Hallett, and R. Hinz, "Real-time markerless rigid body head motion tracking using the microsoft kinect," in Nuclear Science Symposium and Medical Imaging Conference (NSS/MIC), 2012 IEEE. IEEE, 2012, pp. 2241-2246.
J. Duchon, "Splines minimizing rotation-invariant semi-norms in sobolev spaces," in Constructive theory of functions of several variables. Springer, 1977, pp. 85-100.
L. Juan and O. Gwun, "A comparison of sift, pca-sift and surf," International Journal of Image Processing (IJIP), vol. 3, No. 4, pp. 143-152, 2009.
H. Bay, A. Ess, T. Tuytelaars, and L. Van Gool, "Speeded-up robust features (surf)," Computer vision and image understanding, vol. 110, No. 3, pp. 346-359, 2008.
D.G. Lowe, "Object recognition from local scale-invariant features," in Computer vision, 1999. The proceedings of the seventh IEEE international conference on, vol. 2, IEEE, 1999, pp. 1150-1157.
M. Shunbi, Laplace Operator, 2011. [Online; Last Date Accessed: Mar. 14, 2017], http://www.encyclopediaofmath.org/index.php?title=Laplace_operator&oldid=16683.
H. Bay, T. Tuytelaars, and L. Van Gool, "Surf: Speeded up robust features," in European conference on computer vision. Springer, 2006, pp. 404-417.
L.E. Peterson, "K-nearest neighbor," Scholarpedia, vol. 4, No. 2, p. 1883, 2009.
S. Arya, D.M. Mount, N.S. Netanyahu, R. Silverman, and A.Y. Wu, "An optimal algorithm for approximate nearest neighbor searching fixed dimensions," Journal of the ACM (JACM), vol. 45, No. 6, pp. 891-923, 1998.
T. Liu, A.W. Moore, A.G. Gray, and K. Yang, "An investigation of practical approximate nearest neighbor algorithms," in NIPS, vol. 12, 2004, p. 2004.
V. Turau, "Fixed-radius near neighbors search," Information processing letters, vol. 39, No. 4, pp. 201-203, 1991.
P.M. Vaidya, "An o(n logn) algorithm for the all-nearest-neighbors problem," Discrete & Computational Geometry, vol. 4, No. 2, pp. 101-115, 1989.
J.L. Bentley, "Multidimensional binary search trees used for associative searching," Communications of the ACM, vol. 18, No. 9, pp. 509-517, 1975.
R.C. Eberhart, J. Kennedy, et al., "A new optimizer using particle swarm theory," in Proceedings of the sixth international symposium on micro machine and human science, vol. 1. New York, NY, 1995, pp. 39-43.
D. Bratton and J. Kennedy, "Defining a standard for particle swarm optimization," in 2007 IEEE swarm intelligence symposium. IEEEE, 2007, pp. 120-127.
S.A. Khan and A.P. Engelbrecht, "A fuzzy particle swarm optimization algorithm for computer communication network topology design," Applied Intelligence, vol. 36, No. 1, pp. 161-177, 2012.
J. Peng, Y. Chen, and R. Eberhart, "Battery pack state of charge estimator design using computational intelligence approaches," in Battery Conference on Applications and Advances, 2000. The Fifteenth Annual. IEEE, 2000, pp. 173-177.
T. Peram, K. Veeramachaneni, and C.K. Mohan, "Fitness-distance-ratio based particle swarm optimization," in Swarm Intelligence Symposium, 2003. SIS'03. Proceedings of the 2003 IEEE. IEEE, 2003, pp. 174-181.
M. Clerc, "Think locally, act locally: The way of life of cheap-pso, an adaptive pso," Technical Report, http://clerc.maurice.free.fr/pso, Tech. Rep., 2001.
G. Venter and J. Sobieszczanski-Sobieski, "Particle swarm optimization," AIAA journal, vol. 41, No. 8, pp. 1583-1589, 2003.
M. Clerc, "The swarm and the queen: towards a deterministic and adaptive particle swarm optimization," in Evolutionary Computation, 1999. CEC 99. Proceedings of the 1999 Congress on, vol. 3. IEEE, 1999.
F. van den Bergh and A.P. Engelbrecht, "A new locally convergent particle swarm optimizer," in Proceedings of the IEEE international conference on systems, man and cybernetics, vol. 3. IEEE, 2002, pp. 94-99.
G.P. Meyer, S. Gupta, I. Frosio, D. Reddy, and J. Kautz, "Robust model-based 3d head pose estimation," in Proceedings of the IEEE International Conference on Computer Vision, 2015, pp. 3649-3657.

(56) References Cited

OTHER PUBLICATIONS

G.P. Meyer, S. Alfano, and M.N. Do, "Improving face detection with depth," in 2016 IEEE International Conference on Acoustics, Speech and Signal Processing (ICASSP). IEEE, 2016, pp. 1288-1292.
H. Nanda and K. Fujimura, "Visual tracking using depth data," in Computer Vision and Pattern Recognition Workshop, vol. 27, No. 2, 2004, p. 37.
K. Khoshelham, "Accuracy analysis of kinect depth data," in ISPRS workshop laser scanning, vol. 38, No. 5, 2011, p. W12.
S. Izadi, D. Kim, O. Hilliges, D. Molyneaux, R. Newcombe, P. Kohli, J. Shotton, S. Hodges, D. Freeman, A. Davison et al., "Kinectfusion: real-time 3d reconstruction and interaction using a moving depth camera," in Proceedings of the 24th annual ACM symposium on User interface software and technology. ACM, 2011, pp. 559-568.
Y. Chen, Y. Owechko, and S. Medasani, "A multi-scale particle swarm optimization (pso) approach to image registration," 2015.
R.A. Newcombe, S. Izadi, O. Hilliges, D. Molyneaux, D. Kim, A.J. Davison, P. Kohi, J. Shotton, S. Hodges, and A. Fitzgibbon, "Kinectfusion: Real-time dense surface mapping and tracking," in Mixed and augmented reality (ISMAR), 2011 10th IEEE international symposium on. IEEE, 2011, pp. 127-136.
Y. Li, L. Berkowitz, G. Noskin, and S. Mehrotra, "Detection of patient's bed statuses in 3d using a microsof kinect," in 2014 36th Annual International Conference of the IEEE Engineering in Medicine and Biology Society. IEEE, 2014, pp. 5900-5903.
P. Kochunov, J.L. Lancaster, D.C. Glahn, D. Purdy, A.R. Laird, F. Gao, and P. Fox, "Retrospective motion correction in protocol for high-resolution anatomical mri," Human brain mapping, vol. 27, No. 12, pp. 957-962, 2006.
C. Studholme, D.J. Hawkes, and D.L. Hill, "Normalized entropy measure for multimodality image alignment," in Medical Imaging' 98. International Society for Optics and Photonics, 1998, pp. 132-143.
S.B. Gokturk and C. Tomasi, "3d head tracking based on recognition and interpolation using a time-of-flight depth sensor," in Computer Vision and Pattern Recognition, 2004. CVPR 2004. Proceedings of the 2004 IEEE Computer Society Conference on, vol. 2. IEEE, 2004, pp. II-II.
J. You, W. Lu, J. Li, G. Gindi, and Z. Liang, "Image matching for translation, rotation and uniform scaling by the radon transform," in Image Processing, 1998. ICIP 98. Proceedings. 1998 International Conference on, vol. 1. IEEE, 1998, pp. 847-851.
F. Hjouj and D.W. Kammler, "Identification of reflected, scaled, translated, and rotated objects from their radon projections," IEEE Transactions on Image Processing, vol. 17, No. 3, pp. 301-310, 2008.
M. Alhussein and SI. Haider, "Improved particle swarm optimization based on velocity clamping and particle penalization," Third International Conference on Artificial Intelligence, Modelling and Simulation, 2015.
Q. Bai, "Analysis of particle swarm optimization algorithm," Computer and information science, vol. 3, No. 1, pp. 180-184, 2010.
B. Bellekens, V. Spruyt, R. Berkvens, and M. Weyn, "A survey of rigid 3d point-cloud registration algorithms," in Fourth International Conference on Ambient Computing, Applications, Services and Technologies, 2014, pp. 8-13.
J. Blondin, "Particle swarm optimization: A tutorial," from site: http//cs.armstrong.edu/saad/csci8100/pso_tutorial.pdf, 2009.
L.G. Brown, "A survey of image registration techniques," ACM computing surveys (CSUR), vol. 24, No. 4, pp. 325-376, 1992.
N. Chumchob and K. Chen, "A robust affine image registration method," International Journal of Numerical Analysis and Modeling, vol. 6, No. 2, pp. 311-334, 2009.
S. Du, N. Zheng, S. Ying, and J. Liu, "Affine iterative closest point algorithm for point set registration," Pattern Recognition Letters, vol. 31, No. 9, pp. 791-799, 2010.
J. Feldmar and N. Ayache, "Locally affine registration of free-form surfaces," in Computer Vision and Pattern Recognition, 1994. Proceedings CVPR' 94., 1994, IEEE Computer Society Conference on. IEEE, 1994, pp. 496-501.
K. Zielinksi, D. Peters, and R. Laur, "Stopping criteria for single-objective optimization," in Proceedings of the Third International Conference on Computational Intelligence, Robotics and Authonomous Systems, 2005.
A.W. Fitzgibbon, "Robust registration of 2d and 3d point sets," Image and Vision Computing, vol. 21, No. 13, pp. 1145-1153, 2003.
M. Fleder, S. Pillai, and S. Jeremy, "3d object tracking using the Kinect," MIT CSAIL 6.1, p. 870.
J. Han, L. Shao, D. Xu, and J. Shotton, "Enhanced computer vision with microsoft kinect sensor: A review," IEEE transactions on cybernectics, vol. 43, No. 5, pp. 1318-1334, 2013.
P. Henry, M. Krainin, E. Herbst, X. Ren, and D. Fox, "Rgb-d mapping: Using kinect-style depth cameras for dense 3d modeling of indoor environments," The International Journal of Robotics Research, vol. 31, No. 5, pp. 647-663, 2012.
J. Ho, M.-H. Yang, A. Rangarajan, and B. Vemuri, "A new affine registration algorithm for matching 2d point sets," in Applications of Computer Vision, 2007. WACV'07. IEEE Workshop on. IEEE, 2007, pp. 25-25.
Y. Jiang, T. Hu, C. Huang, and X. Wu, "An improved particle swarm optimization algorithm," Applied Mathematics and Computation, vol. 193, No. 1, pp. 231-239, 2007.
V. Kapoor, B.M. McCook, and F.S. Torok, "An introduction to pet-ct imaging 1," Radiographics, vol. 24, No. 2, pp. 523-543, 2004.
K. Khoshelham and S.O. Elberink, "Accuracy and resolution of kinect depth data for indoor mapping applications," Sensors, vol. 12, No. 2, pp. 1437-1454, 2012.
B. Kovacs, "List mode pet reconstruction," in Sixth Hungarian Conference on Computer Graphics and Gemoetry, Budapest, 2012.
W.W. Moses, "Fundamental limits of spatial resolution in pet," Nuclear Instruments and Methods in Physics Research Section A: Accelerators, Spectrometers, Detectors and Associated Equipment, vol. 648, pp. S236-S240, 2011.
P. Padeleris, X. Zabulis, and A.A. Argyros, "Head pose estimation on depth data based on particle swarm optimization," in 2012 IEEE Computer Society Conference on Computer Vision and Pattern Recognition Workshops. IEEE, 2012, pp. 42-49.
P. Panchal, S. Panchal, and S. Shah, "A comparison of sift and surf," International Journal of Innovative Research in Computer and Communication Engineering, vol. 1, No. 2, pp. 323-327, 2013.
H. Park, G.R. Martin, and A. Bhalerao, "Local affine image matching and synthesis based on structural patterns," IEEE Transactions on Image Processing, vol. 19, No. 8, pp. 1968-1977, 2010.
D.P. Rini, S.M. Shamsuddin, and S.S. Yuhaniz, "Particle swarm optimization: technique, system and challenges," International Journal of Computer Applications, vol. 14, No. 1, pp. 19-26, 2011.
H.M. Sahloul, H.J.D. Figueroa, S. Shirafuji, and J. Ota, "Foreground segmentation with efficient selection from icp outliers in 3d scene," in 2015, IEEE International Conference on Robotics and Biomimetrics (ROBIO), IEEE, 2015, pp. 1371-1376.
Y. Shi, and R.C. Eberhart, "Empirical study of particle warm optimization," in Evolutionary Computation, 1999. CEC 99. Proceedings of the 1999 Congress on., vol. 3 IEEE, 1999.
B. Zitova and J. Flusser, "Image registration methods: a survey," Image and vision computing, vol. 21, No. 11, pp. 977-1000, 2003.
C. Studholme, D.L. Hill, and D.J. Hawkes, "An overlap invariant entropy measure of 3d medical image alignment," Pattern recognition, vol. 32, No. 1, pp. 71-86, 1999.
D.W. Townsend, "Combined positron emission tomography-computed tomography: the historical perspective," in Seminars in Ultrasound, CT and MRI, vol. 29, No. 4. Elsevier, 2008, pp. 232-235.
Y. Tu, C. Zheng, C. Yeh, S. Huang, T. Cheng, and M. Ouhyoung, "Real-time head pose estimation using depth map for avatar control," CVGIP, vol. 2, No. 4, p. 6, 2011.
Y. Tu, H.-S. Lin, T.-H. Li, and M. Ouhyoung, "Depth-based real time head pose tracking using 3d template matching," in SIGGRAPH Asia 2012 Technical Briefs. ACM, 2012, p. 13.

(56) References Cited

OTHER PUBLICATIONS

Z.-H. Zhan, J. Zhang, Y. Li, and H.S.-H. Chung, "Adaptive particle swarm optimization," IEEE Transactions on Systems, Man, and Cybernetics, Part B (Cybernetics), vol. 39, No. 6, pp. 1362-1381, 2009.

Written Opinion of the International Searching Authority, dated Jul. 5, 2018, for International Patent Application No. PCT/US2018/026669; 9 pages.

International Search Report issued by the International Searching Authority, dated Jul. 5, 2018, for International Patent Application No. PCT/US2018/026669; 2 pages.

\* cited by examiner

MOTION CORRECTION SYSTEMS AND METHODS FOR IMPROVING MEDICAL IMAGE DATA

CROSS-REFERENCE

The present application is a national stage entry of International (PCT) Patent Application No. PCT/US2018/026669, filed Apr. 9, 2018, which in turn claims the benefit of U.S. Provisional Application Ser. No. 62/483,434, filed on Apr. 9, 2017, titled "MOTION CORRECTION SYSTEMS AND METHODS FOR IMPROVING MEDICAL IMAGE DATA," the disclosure of which are expressly incorporated by reference herein.

FIELD OF THE DISCLOSURE

The present disclosure generally relates to imaging systems, and more particularly, to devices and methods for improving medical image data.

BACKGROUND OF THE DISCLOSURE

Advances in health care technologies have helped physicians make more accurate diagnoses about the health and medical conditions of their patients. A consequence of having better diagnosis is that physicians can decide the best plan of action to treat any disease or health related problem. One of the many tools currently used to diagnose health problems in patients is Positron Emission Tomography/Computed Tomography (PET/CT). PET/CT is an advanced nuclear imaging technique used to obtain information about the structure and metabolic processes of the cells and tissues in the body. PET/CT scans are typically used to detect cancer, heart diseases, brain disorders and diseases of the central nervous system. In addition, when it is used to detect cancer, PET/CT reveals how the cancer is metabolized and whether it has spread to other parts of the body.

Since PET/CT can take 60 minutes or more to acquire images, it is likely that patients will move throughout the imaging process. Furthermore, for pediatric, geriatric and neurodegenerative patients, the motion is often involuntary. These movements create motion-related artifacts which alter the quantitative and qualitative results during the scanning process. The patient's motion causes image blurring, reduction in the image signal to noise ratio, and reduced image contrast, which could lead to misdiagnoses of the patient's medical condition. In some cases, the quality of the obtained images is sufficiently poor to require re-imaging of the patient, which increases the exposure of the patient to harmful ionizing radiation and wastes resources.

It is desirable to develop improved imaging systems and methods to avoid the foregoing problems with existing systems.

SUMMARY OF THE DISCLOSURE

In one embodiment, the present disclosure provides an image motion-correction device having a processor comprising instructions embedded in a non-volatile storage device. The instructions include a frame file generation unit configured to obtain data frames representing motion of a patient, an image correction unit configured to create affine motion matrices representing motion between the data frames. The image correction unit is further configured to obtain medical image files correlated in time to the data frames, and to apply the affine motion matrices to the medical image files. Also, the image correction unit is configured to generate motion-corrected medical image files, and to store the motion-corrected image files.

In one example, the frame file generation unit is further configured to obtain depth map data and to generate unified frame files combining data frames with corresponding depth map data.

In another example, the frame file generation unit is further configured to obtain region of interest data representing a region of interest and to create the affine motion matrices using only data in the data frames corresponding to the region of interest.

In yet another example, the image correction unit is further configured to create the affine motion matrices by registering pairs of data frames in parallel processes to obtain intermediate affine motion matrices representing motions between the data frames in the pairs and to register the data frames to a reference data frame using the intermediate affine motion matrices. In a variation, the image correction unit is further configured to register subsets of the data frames to different reference data frames to compensate for drift.

In still another example, the image correction unit is further configured to create the affine motion matrices by extracting patient features from the data frames and matching the patient features.

In another embodiment, the present disclosure provides a computing device having a processor operative to generate at least one unified frame file base on motion image data, depth map data corresponding to the motion image data, and region of interest data, to generate at least one corrected image file derived from the medical image file by performing the motion correction based on the at least one unified frame file, and to output the at least one corrected image file for display to one or more display devices.

In one example, the at least one processor is further configured to unify the motion image data, the corresponding depth map data, and the region of interest data based on a time stamp for generating the at least one unified frame file.

In another example, the at least one processor is further configured to perform frame registration between consecutive frames of the motion image data. In a variation, the at least one processor is further configured to read the consecutive frames of the motion image data and generate a point cloud associated with the region of interest data based on the image motion data and the depth map data. In a further variation, the at least one processor is further configured to detect and extract at least one feature from the point cloud for generating a matched point cloud based on the detected and extracted at least one feature. In a yet further variation, the at least one processor is further configured to create at least one affine transformation matrix between the consecutive frames of the motion image data based on the matched point cloud using an optimization process. In a still further variation, the at least one processor is further configured to perform model registration for all frames of the motion image data with respect to a reference frame using the at least one affine transformation matrix. In a yet still further variation, the at least one processor is further configured to perform the motion correction on the medical image file based on the at least one affine transformation matrix.

In another variation, the at least one processor is further configured to align chronologically the medical image file and the at least one affine transformation matrix to select which affine transformation matrix is applied against the medical image file. In yet another variation, the at least one processor is further configured to generate a three-dimensional volume of the medical image file based on the selected affine transformation matrix. In still another variation, the at least one processor is further configured to generate the at least one corrected image file based on the three-dimensional volume of the medical image file.

In yet another embodiment, the present disclosure provides a patient scanning system including a patient scanning device including sensors configured to sense signals comprising information regarding internal tissues of the patient, a signal processor to convert the sensed signals into medical image files, a motion detection device to capture data frames representing motion of the patient, and an image motion-correction device as in claim 1 configured to create affine motion matrices representing motion between the data frames and generate motion-corrected medical image files from the medical image files and the affine motion matrices.

In still yet another embodiment, the present disclosure provides a patient scanning system including a patient scanning device including sensors configured to sense signals comprising information regarding internal tissues of the patient, a motion detection device to capture data frames representing motion of the patient, a motion determination device configured to create affine motion matrices representing motion between the data frames, and a signal processor to convert the sensed signals into motion-corrected medical image files using the affine motion matrices.

While multiple embodiments are disclosed, still other embodiments of the present disclosure will become apparent to those skilled in the art from the following detailed description, which shows and describes illustrative embodiments of the present disclosure. Accordingly, the drawings and detailed description are to be regarded as illustrative in nature and not restrictive.

BRIEF DESCRIPTION OF THE DRAWINGS

The features and advantages of the disclosure will become more readily appreciated as the same become better understood by reference to the following detailed description when taken in conjunction with the accompanying drawings, where.

DETAILED DESCRIPTION

Figure 1:
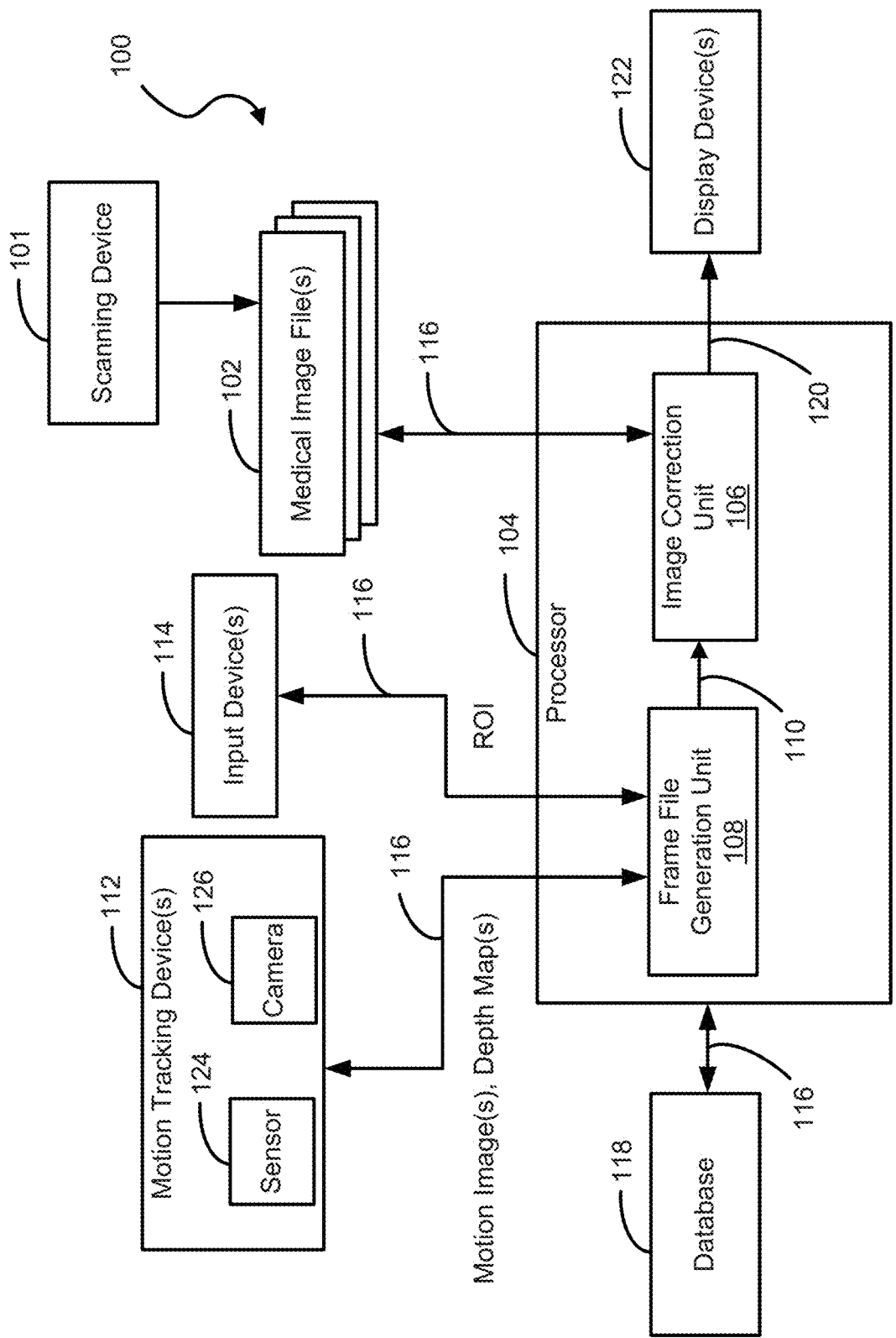
FIG. 1 is a block diagram of an embodiment of an imaging system including a motion correction system.

For the purpose of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

Referring now to FIG. 1, an imaging system is provided to correct the movement artifacts in medical images generated by the motion of the patients inside the medical image scanner. An embodiment of an imaging system, denoted by numeral 100, comprises a scanning device 101 configured to generate medical image files 102, a motion tracking device 112 configured to detect motion of a patient being scanned in scanning device 101, and a processor 104 coupled via a network 116 to scanning device 101, motion tracking device 112, an input device 114, and a database 118. Motion tracking device 112 includes a sensor 124 and a camera 126. Camera 126 captures video of the patient and sensor 124 detects depth. Combined, the video images and the depth data provide three-dimensional (3D) motion information about the patient. Processor 104 includes a frame file generation unit 108 and an image correction unit 106. Frame file generation unit 108 uses the 3D motion information to generate unified frame files 110. Image correction unit 106 uses the unified frame files 110 to improve the quality of medical image files 102 by compensating for the patient's motion. Corrected image files 120 are outputted by image correction unit 106 to a display device 122. In one example, corrected image files 120 comprise motion-corrected DICOM files.

Advantageously, medical image files 102 can be synchronized with the 3D motion information, and the 3D motion information can be used to "extract" motion effects from medical image files 102. The compensated images enable improved diagnosis and reduce the likelihood that the patient will need to be re-imaged to obtain better quality images.

In one embodiment, camera 126 captures infrared images and sensor 124 includes an infrared (IR) emitter and an IR depth sensor, and motion tracking device 112 thereby generates 3D motion information comprised in real-time depth maps and infrared motion image frames. The IR emitter emits infrared light in a "pseudo-random" speckle pattern into a scene. Light reflected from speckles is captured by the IR sensor. The IR sensor can work regardless of the lightning conditions in the scene. Image resolution might be, for example, 512×424 pixels at a 30 fps frame rate. Each pixel in the infrared frame has a 16-bit value which represents IR intensity. Each pixel value in the depth map represents a distance in millimeters that range from 500 mm to 8000 mm, which is the working range of the IR sensor. Sensor 124 employs two techniques: Structure light and Time of Flight (TOF). Structure light is a method of sending a known light pattern, usually grids or horizontal bars, into a scene. Using this method, the pattern deforms when hitting the surface of the objects in the scene, allowing an onboard processor to calculate the depth and surface measurements of the object. A pattern used by sensor 124 for the structure light is a speckle pattern. The infrared frames are generated by capturing the intensity of infrared light that was reflected. TOF is a process of measuring the time it takes light to reflect back to the sensor. To generate the depth maps, the IR sensor measures time used by the infrared light to leave the sensor and return to it and uses the time to calculate the distance to the patient. The depth maps are used to generate a 3D point cloud. The IR sensor and IR emitter may have a 70 degrees horizontal and 60 degrees vertical field of view. In another embodiment, the depth maps may be generated by a plurality of cameras 126 using a triangulation technique. For example, sensor 124 can be two stereo aligned cameras that capture rectified images that can be employed the estimation of the depth using triangulation. Other suitable variations are also contemplated to suit different applications.

In one embodiment, camera 126 may be a color camera capable of capturing video, having a resolution of 1920× 1080 pixels at a frame rate of 30 frames per second (fps). Camera 126 may work in three different color formats: RGBA, GBRA and YUV2. Camera 126 may comprise white balancing, black reference, flicker avoidance and color saturation compensation. An exemplary field of view for camera 126 is 85 degrees horizontal and 54 degrees vertical. Other suitable configurations are also contemplated.

Medical image files include PET/CT, ultrasound, magnetic resonance imaging, and any other images of a patient obtained by known or future developed technologies. Medical image files contain image information including slice images, their location and time stamp. Digital imaging and Communications in Medicine (DICOM) is the standard used in medical imaging to handle, store, print, and transmit the information acquired by medical devices. An open-source library, such as DICOM Toolkit (DCMTK), may be used and is a package that contains a set of libraries and applications whose purpose is to implement part of the DICOM standard. The DCMTK package can be used to manipulate the DICOM files. However, a proprietary software library may be created to perform similar functions.

Processor 104 may comprise one or more central processing unit (CPU), graphics processing unit (GPU), and any other core processing unit. Processor 104 may comprise a single device or a distributed device. One or more units can be selectively bundled as a key software model running on processor 104 having software as a service (SaaS) feature.

Any type of computer network having a collection of computers, servers, and other hardware interconnected by communication channels is contemplated, such as the Internet, Intranet, Ethernet, LAN, Cloud Computing, etc. All relevant information can be stored in database 118, which may comprise a non-transitory data storage device and/or a machine readable data storage medium carrying computer-executable instructions, for retrieval by processor 104.

Operation of system 100 comprises four stages.

Figure 2:
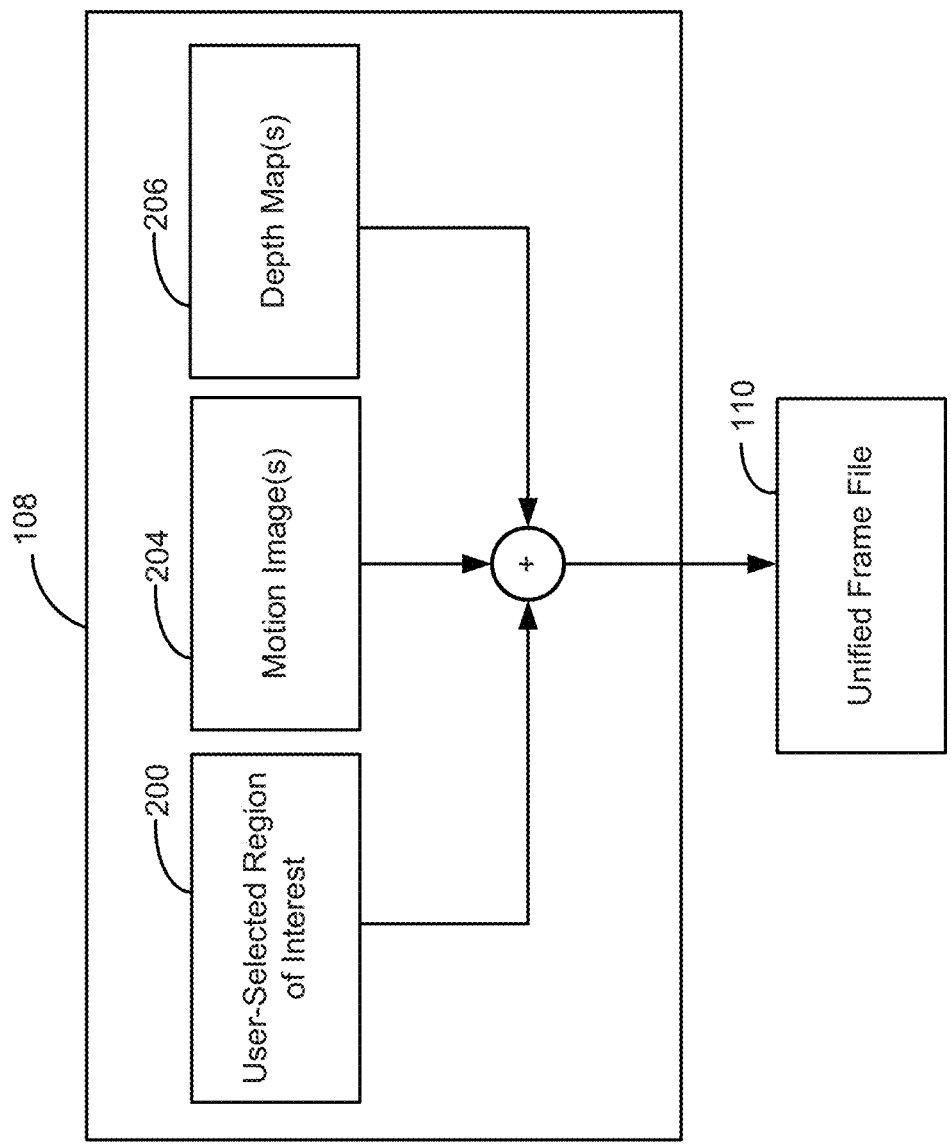
FIG. 2 is a functional block diagram of a frame generation unit of the motion correction system depicted in FIG. 1.

First Stage:

In the first stage, unified frame files 110 are generated from the infrared and depth images. Referring to FIG. 2, frame file generation unit 108 receives infrared motion images 204 (e.g., including data frames representing motion of a patient) and corresponding depth maps 206 from motion tracking device 112, and receives a user-selected ROI 200 from input device 114. Frame file generation unit 108 then processes portions of infrared motion images 204 and depth map 206 corresponding to user-selected ROI 200 to generate a unified frame file 110. Frame file generation unit 108 may run concurrently with timed scanning device 101. Unified frame files 110 are stored in database 118.

More broadly, in some embodiments an image motion-correction processor comprises instructions embedded in a non-volatile storage device configured to obtain motion image data, such as infrared motion images 204, the motion image data representing motion of a patient, depth map data, such as depth map 206, corresponding to the motion image data, and region of interest data, such as user-selected ROI 200; and combine the motion image data, depth map data, and region of interest data, into a unified frame file 110.

In one embodiment, infrared motion images 204 and depth maps 206 are transmitted from motion tracking device 112 through two arrays, where each entry in the array represents the value of the pixel for the corresponding image. Motion tracking device 112 creates both images simultaneously and with the same resolution. Unified frame file 110 is created by simultaneously reading the same position in each array, and writing the values in the corresponding entry of the output file.

An example motion tracking device 112 comprises a MICROSOFT KINECT motion detection system. A KINECT software development kit can be used to extract information from the motion detection system. An Open Source Computer Vision (OpenCV) library can be used to extract and match features in the infrared images obtained from the KINECT motion detection system. An Open Graphics Library (OpenGL) can be used to render 2D and 3D vector graphics and manipulate point clouds using the depth maps obtained from the KINECT motion detection system.

Performance of the system depends on the amount of data that must be processed, which depends on the image sizes. The amount of data captured during a PET scan is defined by the following expression:

$$dataSize = t_{scan} * \frac{frames}{sec} * \frac{1 \text{ MB}}{frame}$$

where $t_{scan}$ is the duration of the PET scan in seconds. A PET scan can last 15-60 minutes (900-3,600 seconds). At a 30 fps acquisition frame rate, the amount of data captured by motion tracking device 112 will be between 26 and 105 GB for a 1 Mb image frame. In one example the frame size is 4.3 Mb, resulting in about 113 to 450 Gb of data. The data determines the amount of processing required in subsequent stages. Hardware also limits throughput. The memory write speed, write latency, and algorithm running time create storage bottlenecks. Unfortunately the majority of this data is redundant. It is therefore desirable to reduce the amount of captured data.

In some embodiments, a user may select a region of interest (ROI) in the patient to reduce the amount of processing. To select the ROI, the user uses input device 114 to mark an area in an image captured by motion tracking device 112. Thereafter only the ROI is used to compute motion parameters. In one variation of the present embodiment, input device 114 is a graphical user interface (GUI) having a plurality of control tabs configured for communicating operating parameters to and from processor 104. The GUI provides a camera tab configured to allow a user to control capture of the infrared images and the depth maps and to select the ROI. A camera window presents in a display the infrared images obtained by motion tracking device 112 in real-time as a video stream. The user selects the ROI using a pointer (e.g., a rectangle). The pointer can be resized and moved within margins of the image while camera 126 is not capturing images (e.g., either, before motion tracking device 112 starts image acquisition or while acquisition is paused). The coordinates of the ROI are then included in the unified frame file 110.

For each acquired frame, an output is a unified frame file 110 which unifies infrared and depth information as well as information of the ROI defined by the user. Unified frame file 110 includes an entry for the ROI and 217,088 entries for the infrared and depth data (corresponding to 512×424 resolution). The ROI entry includes x and y coordinates of the upper left corner of the ROI 200 and the width and height of the ROI. Pixel coordinates on the x-axis vary from 0 to 511. Pixel coordinates on the y-axis vary from 0 to 423. Infrared pixel values vary from 0 to 65,535. Depth values vary from 0 to 8,000.

Figure 3:
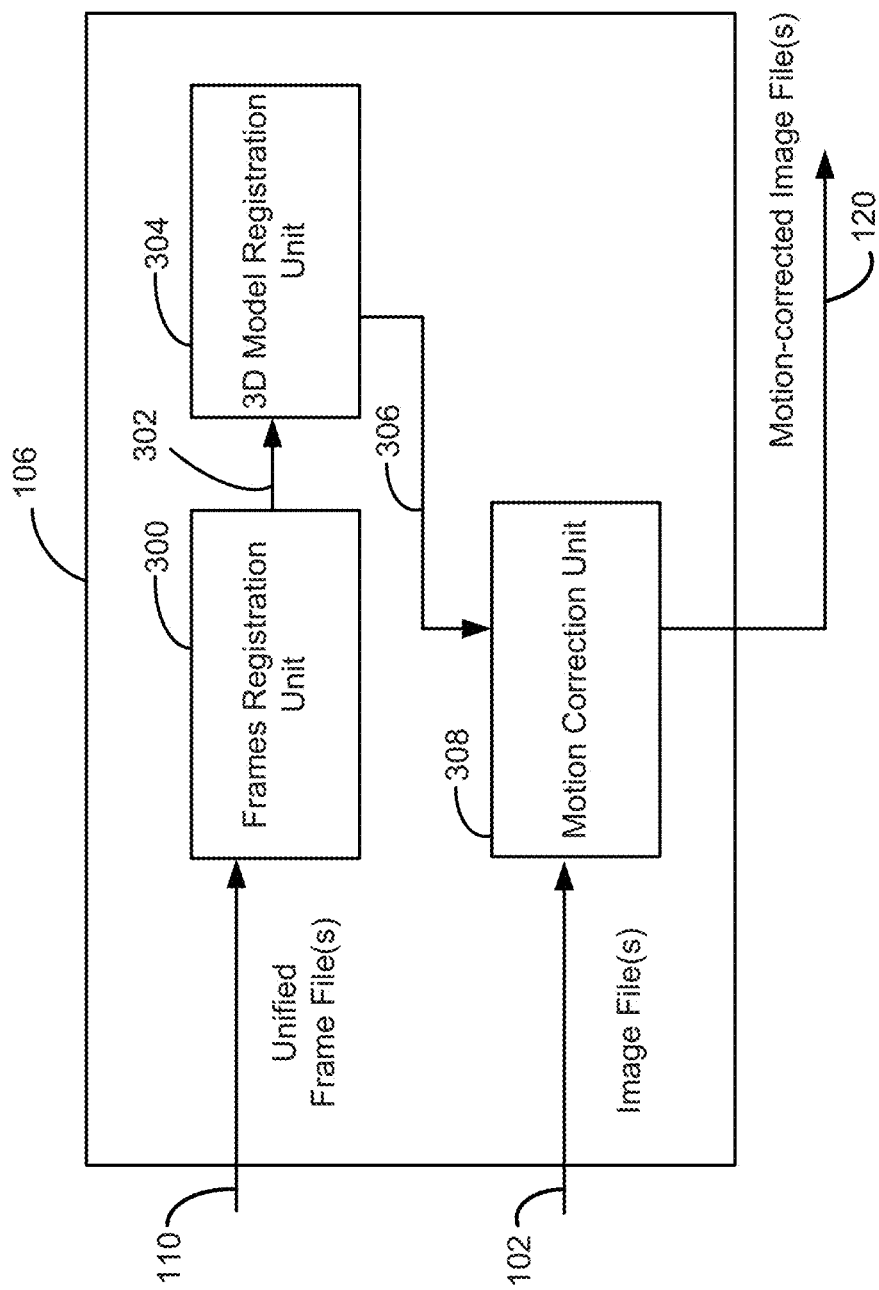
FIG. 3 is a functional block diagram of an image correction unit of the motion correction system depicted in of FIG. 1, featuring a frames registration unit, a 3D model registration unit, and a motion correction unit.

Referring now to FIG. 3, image correction unit 106 includes a frames registration unit 300, a 3D model registration unit 304, and a motion correction unit 308. These units execute the functions of the second, third and fourth stages. In one embodiment, frames are registered sequentially in order. In another embodiment, frames registration unit 300 creates a four-dimensional (4D) model (e.g., x-axis, y-axis, z-axis and time) based on unified frame file 110 that shows little or no movement relative to a 4D model with motion. In the present embodiment, the process of registration of frames is parallelized. In one process, performed in the second stage, consecutive frames are registered. There is no prior information linking the two consecutive frame files. In addition, the only relationship between the infrared images and the depth maps is that the objects present in the scene occupy the same position in both images. In another process, performed in the third stage, the frames are registered to an initial reference frame. Dividing the registration process according to the present embodiment reduces the runtime of system 100.

Figure 4:
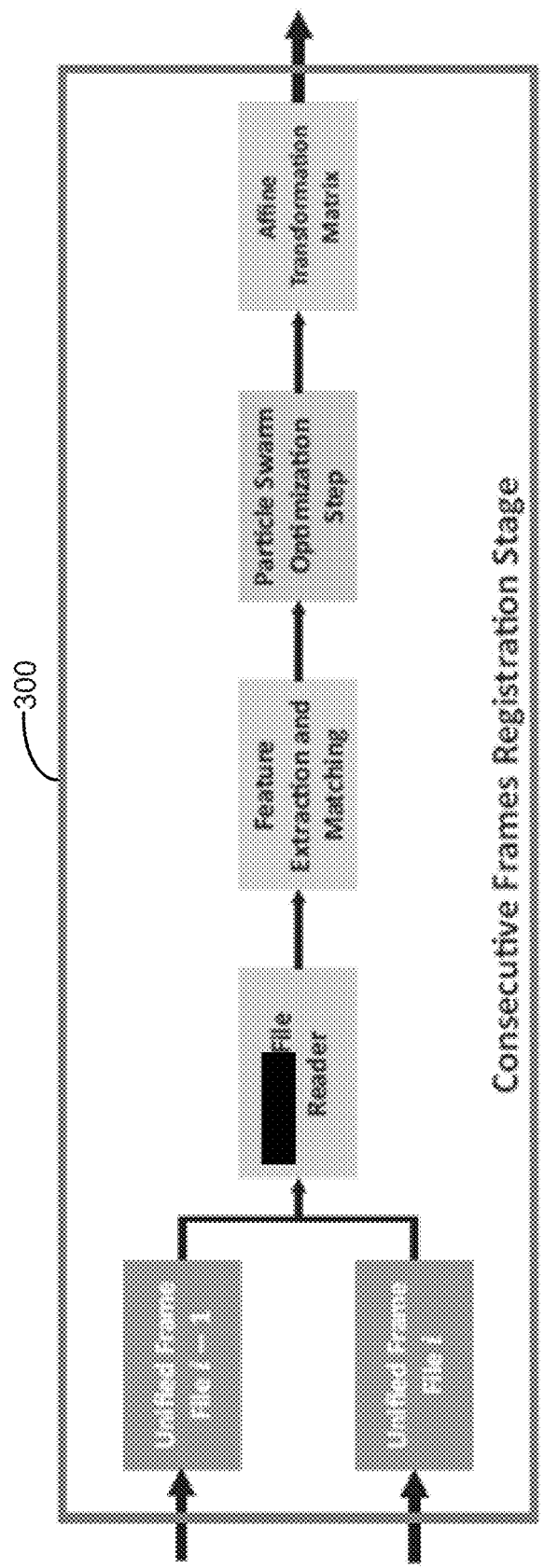
FIGS. 4-7 are functional block diagrams of frames registration stages of the frames registration unit described with reference to FIG. 3.

Second Stage:

In the second stage, processor 104 registers consecutive image frames by extracting and matching features from the images. Referring now to FIG. 4, frames registration unit 300 takes as input n frame files 110 and outputs n−1 affine transformation matrices 302 (e.g., using affine motion matrices representing motion between data frames), which is the maximum number of consecutive pairs of files. FIG. 4 illustrates the steps performed to obtain an affine transformation matrix between a pair of unified frame files i and i−1. In one variation of the present embodiment, frames registration unit 300 performs three steps. In the first or file reader step, frame files 110 are used to generate the infrared images and the point clouds of the ROI. This step is described with reference to FIG. 5. In the second step, the infrared images and the point clouds are used to generate a pair of matched arrays. In the third step, an affine registration is performed using Particle Swarm Optimization (PSO) over the matched arrays. Since the PSO algorithm only requires the two consecutive frame files to obtain the affine transformation matrix, multiple registration processes can be run in parallel, leading to an improvement in the run time of system 100.

The PSO algorithm guides a population of particles, called a swarm, through a multi-dimensional solution space until a potentially optimal solution is reached. Each particle represents a candidate solution. The success of each particle influences the actions of the swarm. A PSO algorithm is one example of an evolutionary computation technique. Other known techniques that include commonly used optimization techniques may also be used to obtain the affine transformation matrix between two consecutive frame files.

Figure 5:
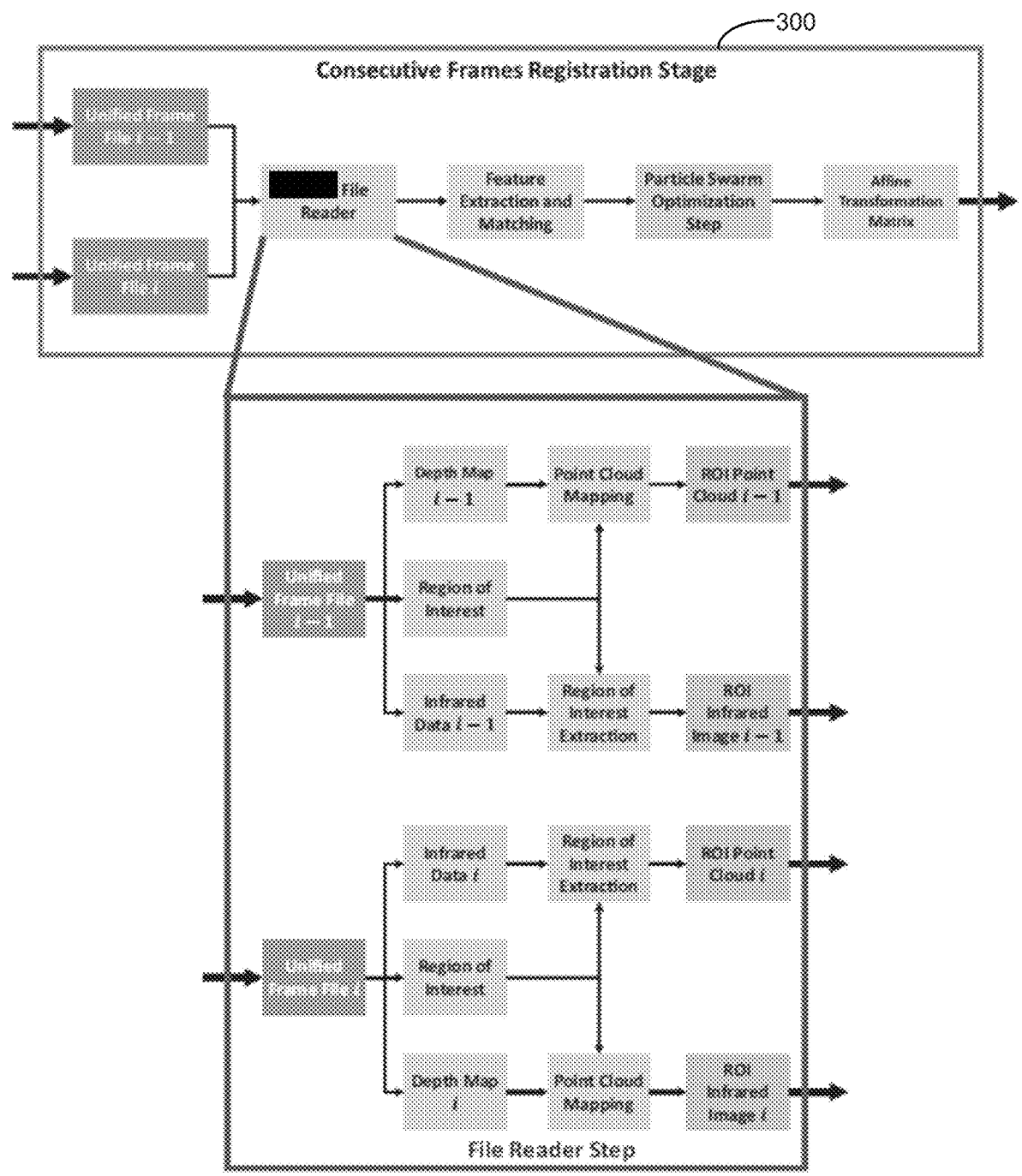

Referring now to FIG. 5, the purpose of the file reader step is to read the unified frame file and create the infrared image and the point cloud of the ROI. The ROI is used to create a mask image where pixel locations corresponding to the ROI comprise is and others are 0s. Each frame file contains this information. To generate the infrared images, the frame file is multiplied by the mask image.

The point clouds are generated using the depth maps. The depth maps are created using the same logic used to create the infrared images. Since it is simpler to apply the mask image to a 2D image, the depth map is multiplied with the mask image to extract a point cloud of the ROI. Each pixel in the ROI depth map generates a point in the point cloud. Using equations 3.2, 3.3 and 3.4, the 3D coordinates of these points are obtained.

$$x_i = \left(\frac{u_i - c_x}{f_x}\right) * (pixel_{u,v}) \qquad (3.2)$$

$$y_i = \left(\frac{v_i - c_y}{f_y}\right) * (pixel_{u,v}) \qquad (3.3)$$

$$z_i = pixel_{u,v} \qquad (3.4)$$

where:

$u_i$ and $v_i$ are the x and y coordinates of the i-th pixel in the depth map;

$pixel_{u,v}$ is the value of the i-th pixel in the depth map;

$f_x$ and $f_y$ are the horizontal and vertical focal length of sensor 124;

$c_x$ and $c_y$ are the location of the center point of sensor 124; and $x_i$, $y_i$ and $z_i$ are the 3D coordinates of the i-th entry of the point cloud.

Each entry of the point cloud is linked to its corresponding pixel in the infrared image. As shown, this step generates point clouds i and i−1 and infrared images i and i−1, all corresponding to the ROI. The SDK instruction GetDepthCameraIntrinsics( ) obtains the values of $f_x$, $f_y$, $c_x$ and $c_y$. A depth value varies from 0 to 8,000, which represents the distance, e.g., in centimeters or millimeters, of sensor 124 to the patient.

Figure 6:
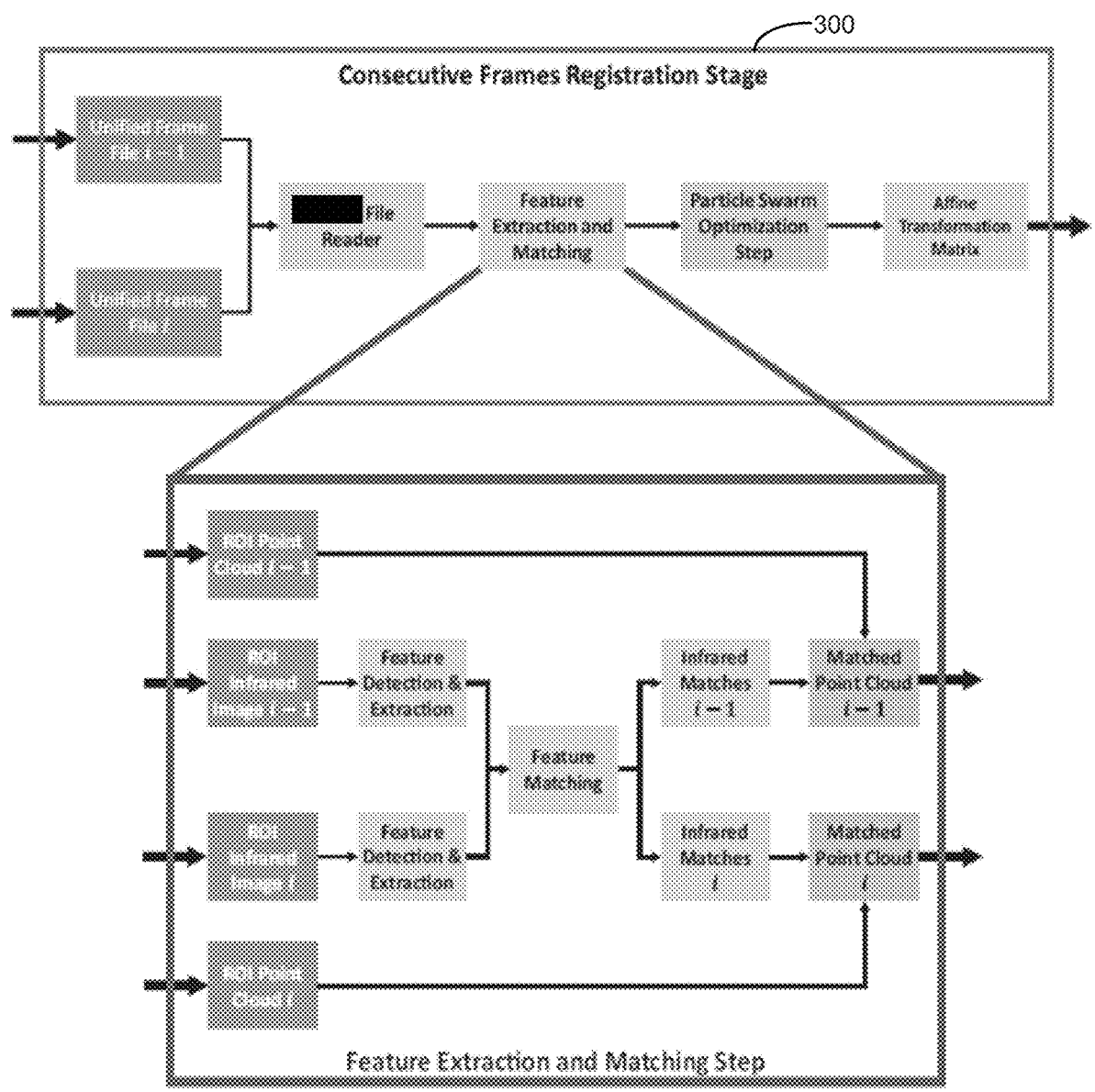

Referring now to FIG. 6, the purpose of the features extraction and matching shown in FIG. 4 is to generate a pair of matched arrays. Advantageously this implementation does not require information about surrounding objects or initialization. Any features extraction algorithm may be used to identify features in the infrared images. Examples of feature extraction techniques include Speeded-Up Robust Feature (SURF), Scale-Invariant Feature Transform (SIFT), and Histogram of Oriented Gradients (HOG). Once the features are extracted, system 100 proceeds to obtain the matches between both images using the features. Any features matching algorithm may be used. An example feature matching algorithm is the nearest neighbor search library called Fast Approximate Nearest Neighbor Search (FLANN), which is implemented in OpenCV. This library was developed with the purpose of matching features in a fast and efficient manner. The algorithm implemented in this library takes two features arrays (source and reference) and creates a k-d tree of each array. A k-d tree is a data structure used to arrange the points in a k-dimensional space. These structures are useful for applications that involves a multi-dimensional search, such as in nearest neighbor searches. To perform the feature matching process, the method takes a feature of the source array and it finds its nearest neighbor in the reference array by performing a query in the k-d tree. This process is repeated for each feature in the source array. The matches returned by the FLANN implementation are passed through an outliers removal step. If the distance between two matched features is considerably large, the match is considered an outlier. The mean and the standard deviation of the distances of all the matches will be calculated and matches whose distance is larger than the mean plus the standard deviation are removed. The remaining matches are used in the next step. This behavior is described in Equation 3.5.

$$O(M_i) = \begin{cases} \text{true,} & \text{If } d_i \geq \bar{d} + \sigma_d \\ \text{false,} & \text{Otherwise} \end{cases} \quad (3.5)$$

where, $O(M_i)$ is the function that determines if the matched features i is an outlier $F_i$ is the i-th matched features $d_i$ is the distance between these features d is the mean of the distances of all the matches.

$\sigma_d$ is the standard deviation of the distances of all the matches.

The last step of this stage is dedicated to the creation of the arrays used by the PSO algorithm. Each element of the matched features array represents a match and it includes two entries. The first entry is the location of a feature in the source infrared image and the second entry is the feature in the reference image. To generate the matched point clouds, the features entries in the matched features array are located in their respective depth maps, then, a n-by-n square kernel is placed around each coordinate. All non-zero distance values of the pixels inside this area are averaged. Using the mean distance value and the 2D coordinates of the feature, the value of the 3D coordinates can be obtained using Equations 3.2, 3.3 and 3.4. These coordinate values represent the corresponding matched feature in the point cloud. These values are then saved in the same position number on the output point clouds arrays. The process is repeated with each element of the matched features array and the output generates two point clouds arrays whose entries represent the matched features of the infrared image in 3D. To choose the kernel size, tests were performed using the complete implemented system while the kernel size value was varied. An exemplary value for the kernel size is 21, which was obtained based on an average distance and standard deviation of the matches at the output of the system while varying the kernel size.

Figure 7:
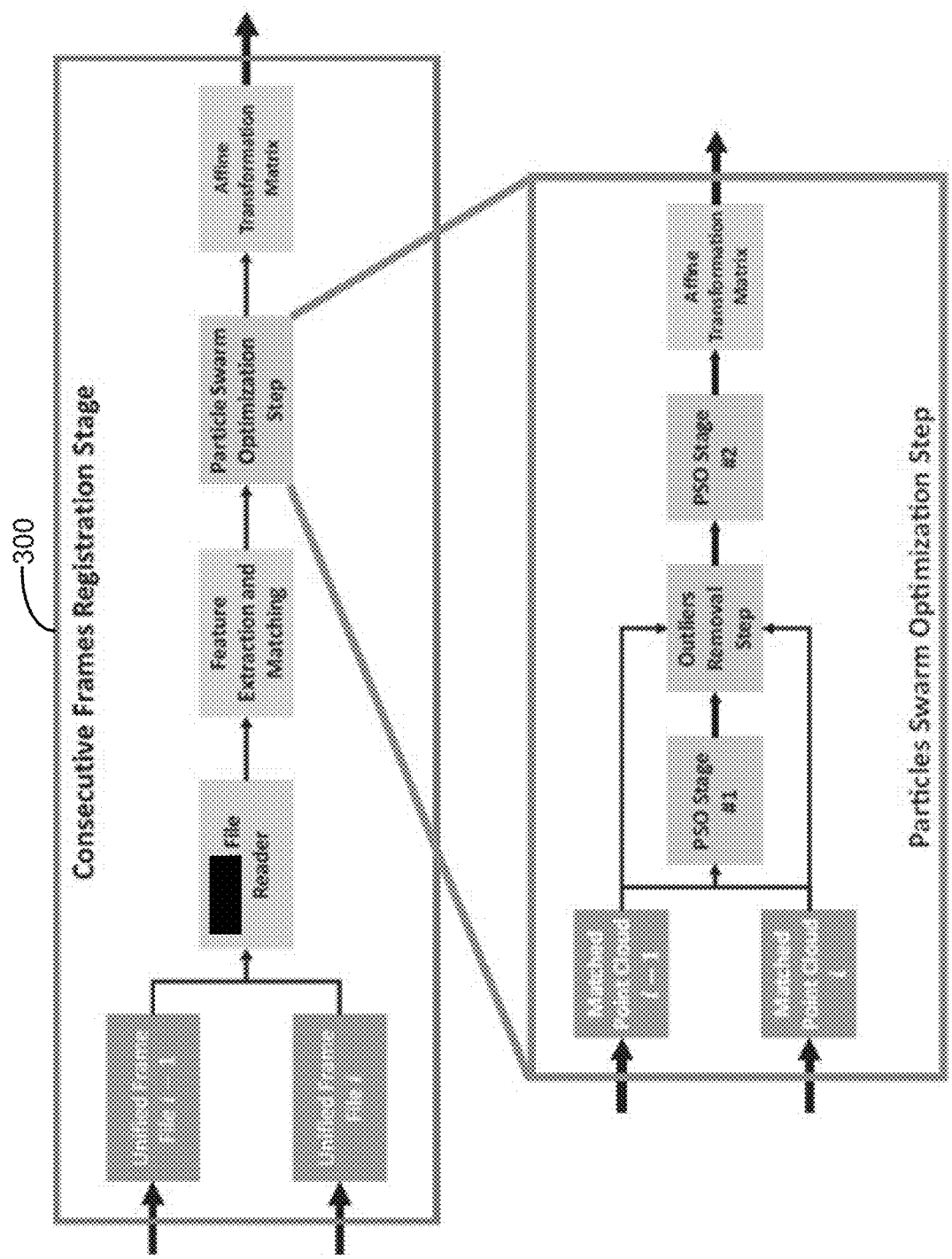

Referring now to FIG. 7, the PSO step of FIG. 4 is used to obtain the 3D affine transformation matrices between consecutive frames. A first PSO stage has as inputs the two matched point clouds. The output is a 3D affine transformation matrix. The outlier removal step takes the two point clouds (source and reference) and the 3D affine matrix and returns the two point clouds with the outliers entries removed. A second PSO stage is then performed resulting in a final 3D affine transformation matrix. In the previous outliers removal step, an outlier was any match whose distance is higher than the mean of all the matches' distances plus the standard deviation of all the matches' distances (Equation 3.5). The same concept is applied in the outlier removal step between the two PSO steps, except that the comparison uses the mean and the standard deviation of the distances between the corrected features. In the case in which the features are perfectly aligned with their reference, the distance between the corrected input feature and its reference feature will be 0. On the other hand, if the distance between the corrected input feature and its reference feature increases with respect to the distance between the uncorrected features, then it means that the matched feature is potentially an outlier because the input feature is moving away from the reference instead of moving closer to the reference. Therefore, in this outlier removal step, the distances between the corrected source point cloud and the reference point cloud are used to obtain the mean and the standard deviation used in Equation 3.5, instead of the distance between the source point cloud and the reference point cloud.

In an embodiment of a PSO algorithm, the PSO algorithm (a) initializes parameters; (b) compute an initial fitness value; (c) if the initial fitness value is 0 then returns an identity matrix as the result; (d) initialize particles; (e) while the stop criteria is not met, increase an iteration counter and for each particle, defines the best local particle of the particles in the neighborhood; (f) for each dimension of the particle computes the inertia weight and the velocity of the dimension; (g) applies the particle to pointCloud1 and computes the new fitness value; (h) updates the particle's best local fitness value; (i) updates the best global fitness value; (j) checks if the stop criteria is met and (k) returns the best global particle as the affine transformation matrix. Each particle represents a possible affine matrix that aligns both point clouds arrays, which means that each particle has 12 degrees of freedom. The fitness function chosen for this system is the sum of the distances between the corrected and reference features described by Equation 3.6.

$$\text{fitness} = \sum_{i=1}^{n} \sqrt{\begin{array}{c}(x_{PC1,i} - x_{PC2,i})^2 + (y_{PC1,i} - y_{PC2,i})^2 + \\ (z_{PC1,i} - z_{PC2,i})^2\end{array}} \quad (3.6)$$

where, n is the number of matches.

PC1 and PC2 are pointCloud1 and pointCloud2, respectively.

$x_{A,i}$, $y_{A,i}$ and $z_{A,i}$ are the x, y and z coordinates of the i-th feature in point cloud A.

For a perfect match the fitness value will be equal to 0. Therefore, the smaller the value of the fitness function, the better the results of the registration. In some rare occasions, the patient may remain immobile for some time. This implies that the respective frames will reflect no motion, which means that the affine transformation matrix between those frames is approximately an identity matrix. An initial fitness value is calculated to prevent the algorithm from running unnecessarily. If the initial fitness value is equal to 0, the algorithm considers that there was no movement between the two frames and returns an identity matrix as the result. The update of the position of each dimension of the particle is done using Equation 2.24. The velocity of each dimension of the particle is updated using Equation 2.36. Meanwhile, the inertia weight term is calculated using Equation 2.41.

$$x_i(t+1) = x_i(t) + v_i(t+1) \quad (2.24)$$

where $x_i(t)$ is the position of particle i in the solution space at time step t, and $v_i(t)$ is the velocity term for the particle i at time step t.

$$v_i(t+1) = wv_i(t) + c_1 r_1(t)[\text{pbest}_i(t)] + c_2 r_2(t)[B\text{best}(t) - x_i(t)] \quad (2.36)$$

where:
w is an inertia weight value,
$v_i(t)$ is the velocity of particle i at time t,
c1 and c2 are acceleration constants,
$r_1(t)$ and $r_2(t)$ are two random values updated with each iteration,
$x_i(t)$ is the position of the particle i at time t,
$\text{pbest}_i$ is the particle i best position,
Bbest(t) is defined as:

$$B_{best}(t) = \begin{cases} s_{best}(t) & \text{for } gbest \text{ PSO} \\ l_{best}(t) & \text{for } lbest \text{ PSO} \end{cases} \quad (2.30)$$

$s_{best}(t)$ is the swarm best position at time t for global best particle swarm optimization.
$l_{best}(t)$ is the best position of the neighborhood at time t for local best particle swarm optimization.

$$w_i(t+1) = w(0) + (w(n_i) - w(0)) \frac{e^{m_i(t)} - 1}{e^{m_i(t)} + 1} \quad (2.41)$$

where: $w(0) < 1$, $w(n_i) \approx 0.5$, and $m_i$ is the relative improvement and it is estimated as:

$$m_i(t) = \frac{f(l_{best,i}(t)) - f(x_i(t))}{f(l_{best,i}(t)) + f(x_i(t))} \quad (2.42)$$

Clerc's approach, which is one embodiment of PSO asserts that as an individual improves more over its neighbors, it should be able to follow its own path.

The initialization step is in charge of generating the initial particles. Each particle is assigned an identification label, which is its index inside an array. Then, the swarm is initialized using a completely random normal distribution, and a random value is assigned to each of the 12 degrees of freedom of each particle. Also, this step has the task of initializing the internal variables used by the algorithm, such as: the particles' velocity array, the best local fitness for each particle, the best local result for each particle and the best global particle.

The acceleration coefficients $c_1$ and $c_2$ are equal to 1.49. A maximum number of iterations is used to ensure that the algorithm has a breakpoint. To determine its value, the execution time of a single iteration is taken into consideration, which is on average 0.807±0.2118 ms. Based on experiments, it was assigned that the algorithm should not take more than 30 seconds per file in the worst-case scenario. Thus, the maximum number of iterations is: 30/(0.807+0.2118)=29,447.87, which is approximately 30,000 iterations. An exemplary range of a swarm size is between 20 and 30 particles, which gives a good balance between runtime and number of iterations with neighborhood sizes ranging from 15% to 30% of the swarm size.

Figure 8:
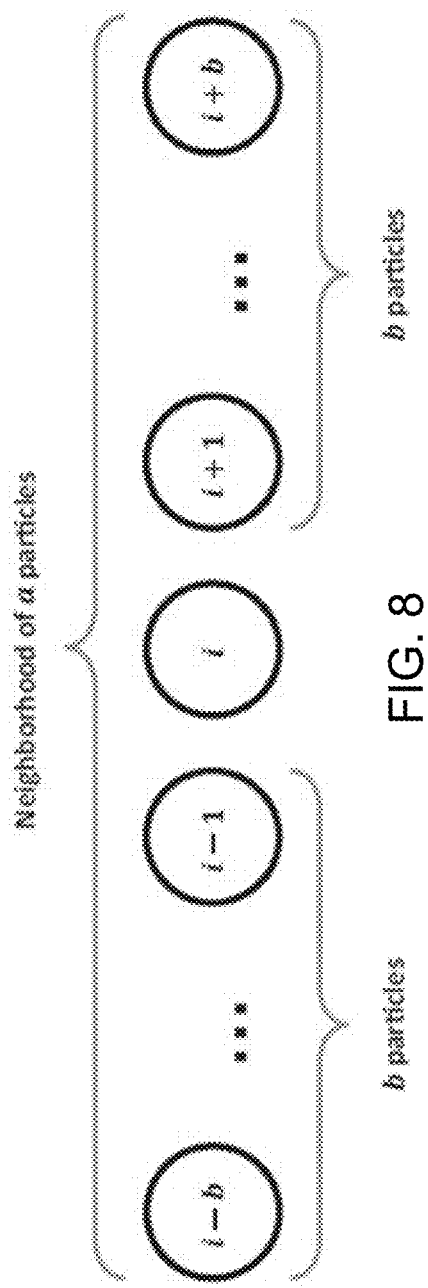
FIG. 8 is a schematic diagram of a neighborhood size described with reference to a particle swarm optimization technique implemented by the motion correction system of FIG. 1.

Referring now to FIG. 8, an exemplary neighborhood size is shown for particle i. In one variation, a swarm size of 30 particles and a neighborhood size, Nsize, of 11 particles were used with good results. During each iteration, each particle has its "own" neighborhood which is made up of Nsize−1 particles. For example, for particle i, its neighborhood includes all particles between $$i - \frac{Nsize - 1}{2} \text{ and } i + \frac{Nsize - 1}{2}.$$

Each particle in the neighborhood communicates its results to particle i, which compares who has the best results based on the fitness value, but it does not communicate this to its neighbors. It uses the obtained best result as the $B_{best}(t)$ which is needed to update its own position. The algorithm has two stopping conditions: the first condition is that the maximum number of iterations is met and the second condition is that the difference between the last change and the average of the last 10 changes is less than 1/1,000,000. Also, the algorithm works in a synchronous way, which means that, in each iteration, all particles must update their positions before communicating their results to the swarm.

Figure 10:
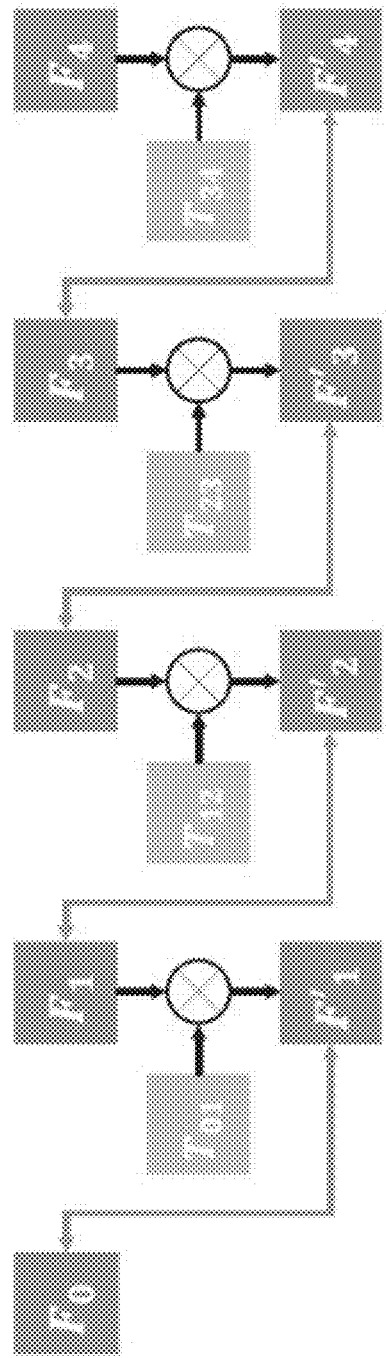
Figure 9:
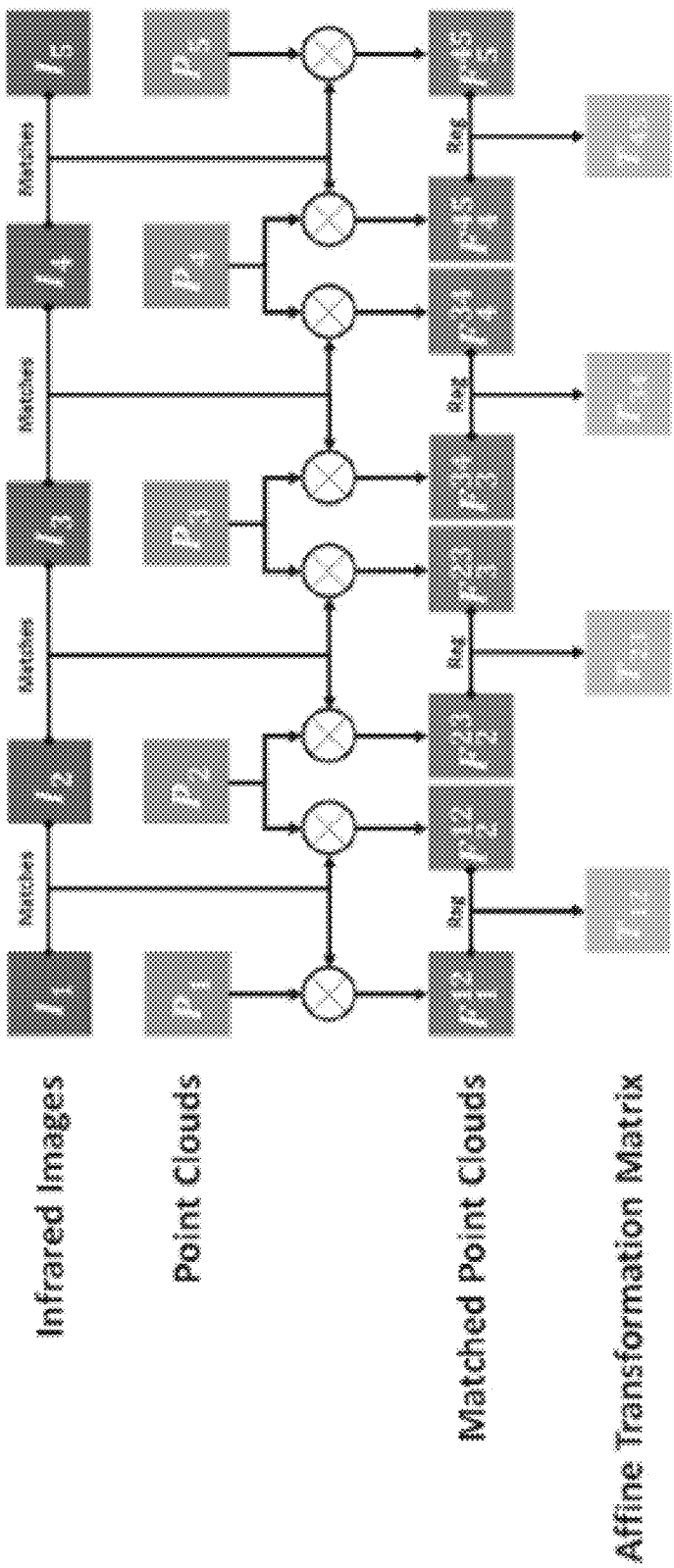
FIGS. 9 and 11 are functional block diagrams of an embodiment of a 3D model registration stage of the 3D model registration unit of FIG. 3.
Figure 11:
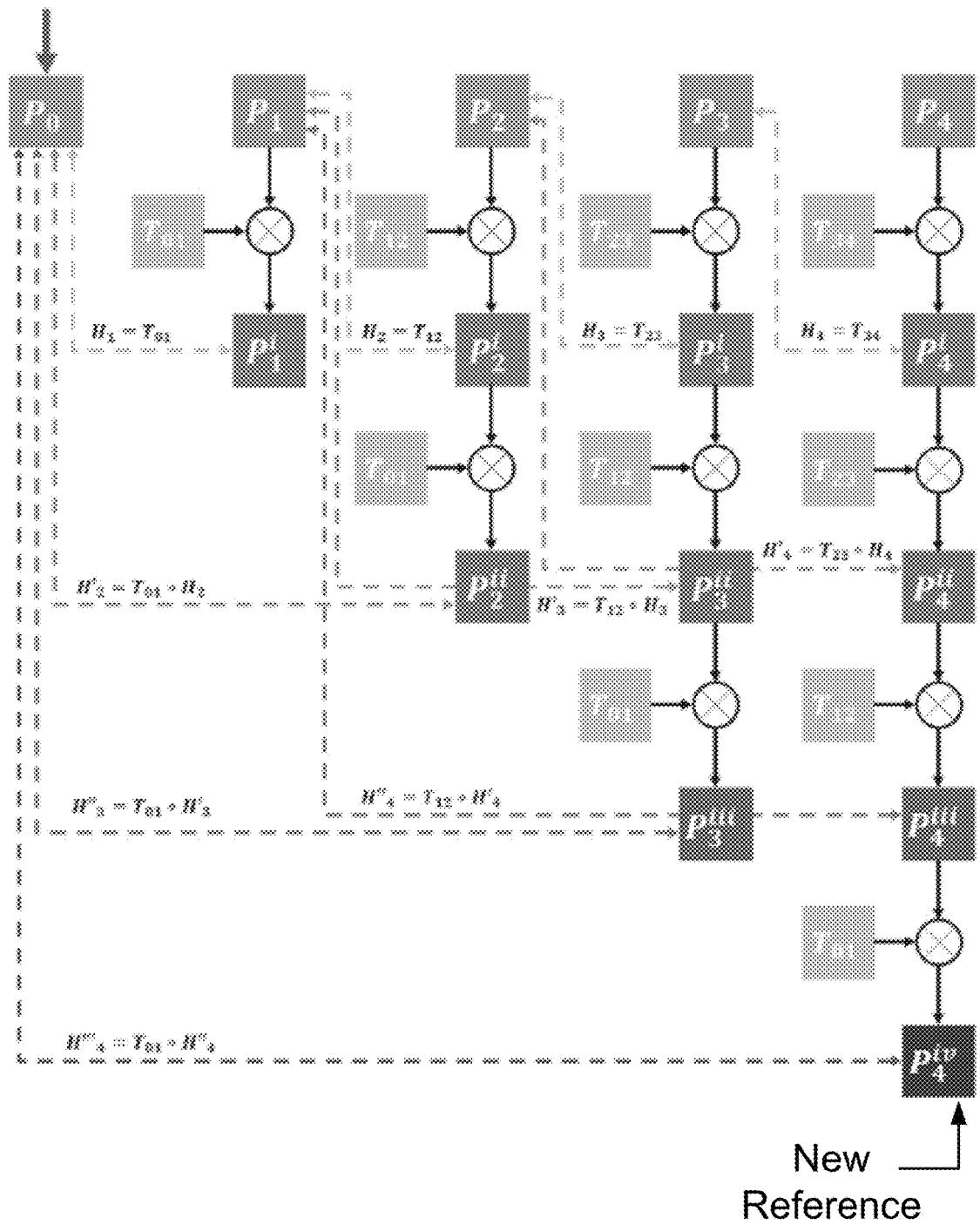

Third Stage:

Referring now to FIGS. 9-11, exemplary steps of 3D Model Registration unit 304 are shown. In the previous stage, only the affine matrices that align consecutive frames were obtained. However, to perform motion correction, all frames must be aligned with respect to an initial reference frame. In the present stage, the affine matrices from the previous stage are used in addition to the frame files. FIG. 9 illustrates the process by which the infrared images and point clouds have passed to this point of present system 100. The first step is to obtain the features matches between the infrared images $I_{i-1}$ and $I_i$. Then, the matches and the point clouds are used to generate the matched point clouds, which are used to perform the registration and the result is the affine matrix $T_{(i-1)i}$ which aligns point cloud i and point cloud i−1. In the case where perfect registration is obtained, whenever the resulting affine matrix $T_{(i-1)i}$ is applied to point cloud i, it will generate point cloud i−1. Therefore, to obtain the affine matrix Tot, which aligns point cloud i and point cloud 0 (the initial reference), it is enough to apply all the affine matrices sequentially starting with $T_{(i-1)i}$ and ending with $T_{01}$. FIG. 10 illustrates this concept, where $F_i$ is the original point cloud and $F_i'$ is the registered version of $F_i$ with respect to the point cloud If the point cloud are perfectly aligned, $F_i'$ and $F_{i-1}$ will be equal. Then, for example, to align $F_2$ with the reference, first apply $T_{12}$ to $F_2$ which gives $F_2'=F_1$, then apply $T_{01}$ to $F_2'$ which gives $F_2''=F_1'=F_0$.

Even small differences in the transformation may cause a registration error. If the procedure described above is applied, these errors may accumulate along the frames causing a drifting behavior as more affine matrices are applied. In a variation of the present embodiment, to reduce the drifting effect due to the errors, a windowing method is used to update the reference frame after k number of frames have been processed. FIG. 11 illustrates the workflow of the proposed algorithm for a K=4. The first step of the algorithm is to perform the registration between frames i and i−1. This step is performed in the previous stage.

Once this task is done, the algorithm has to perform the registration between corrected frame i and frame i−2 using the 2 previous frames that have not been corrected with respect to the reference frame. This is further carried out using all the previous i−1 frames that have not been corrected with respect to the reference frame, and the entire process repeated until all the frames in the window of size K are registered with respect to the reference frame. Once all frames have been corrected, frame K is set as a new reference frame for the next set of frames. The value of K can vary depending on the amount of drift.

Figure 12:
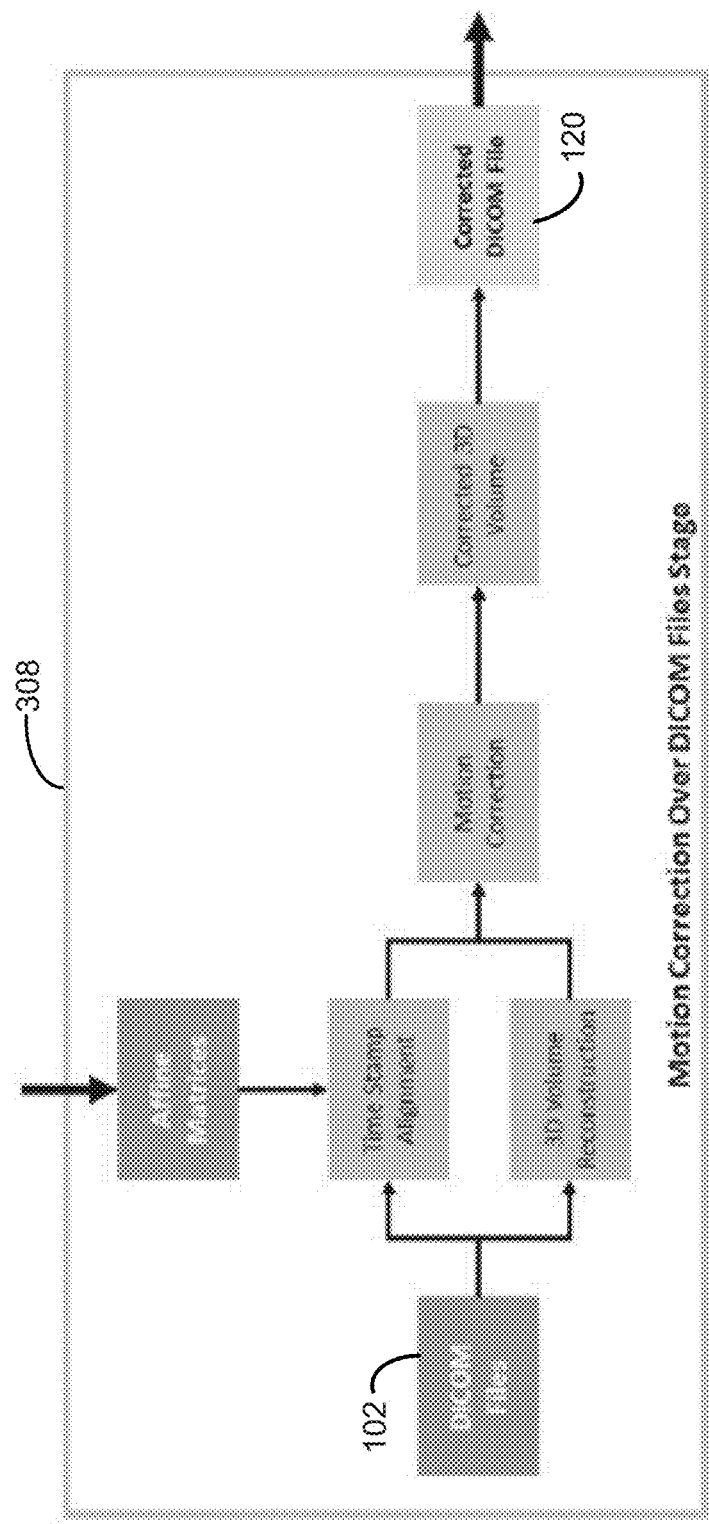
FIG. 12 is a functional block diagram of another embodiment of a motion correction stage of the motion correction unit of FIG. 3.
Figure 13:
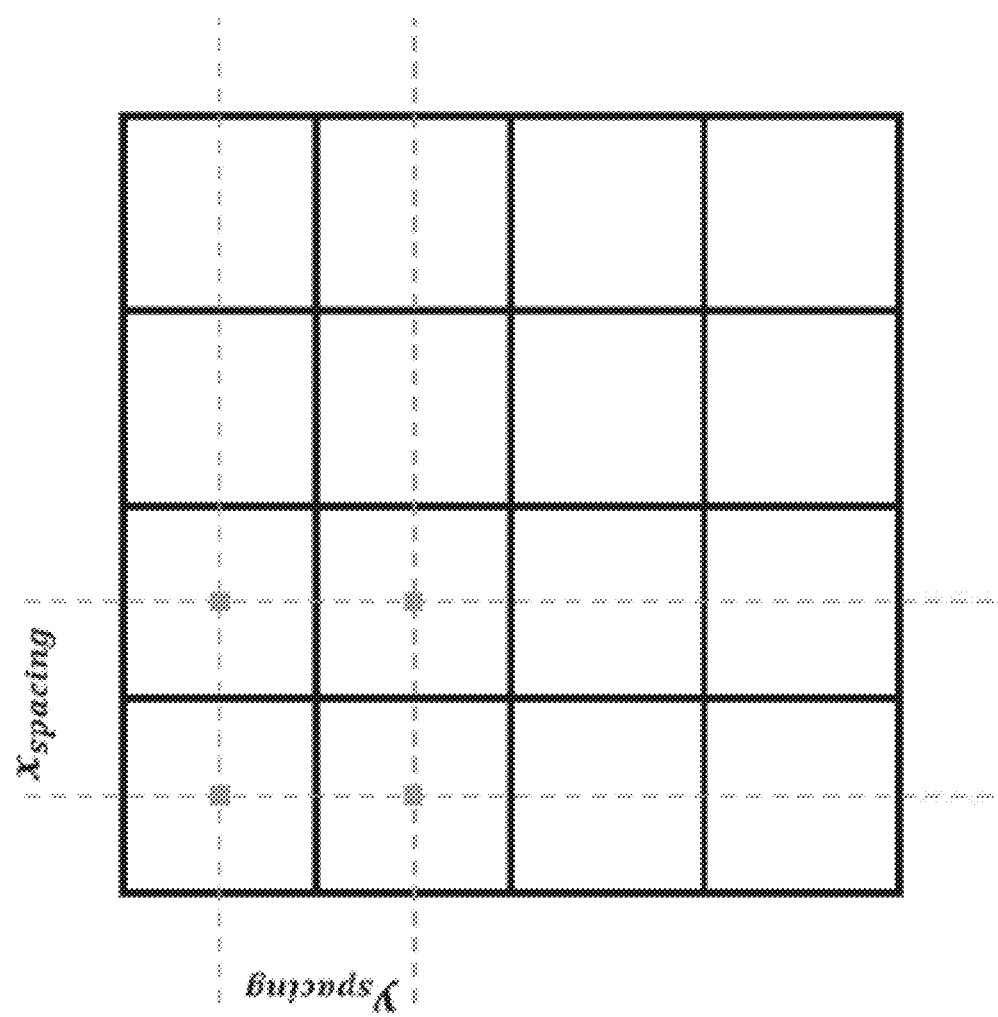
FIG. 13 is a pictorial representation of pixel spacing.
Figure 14:
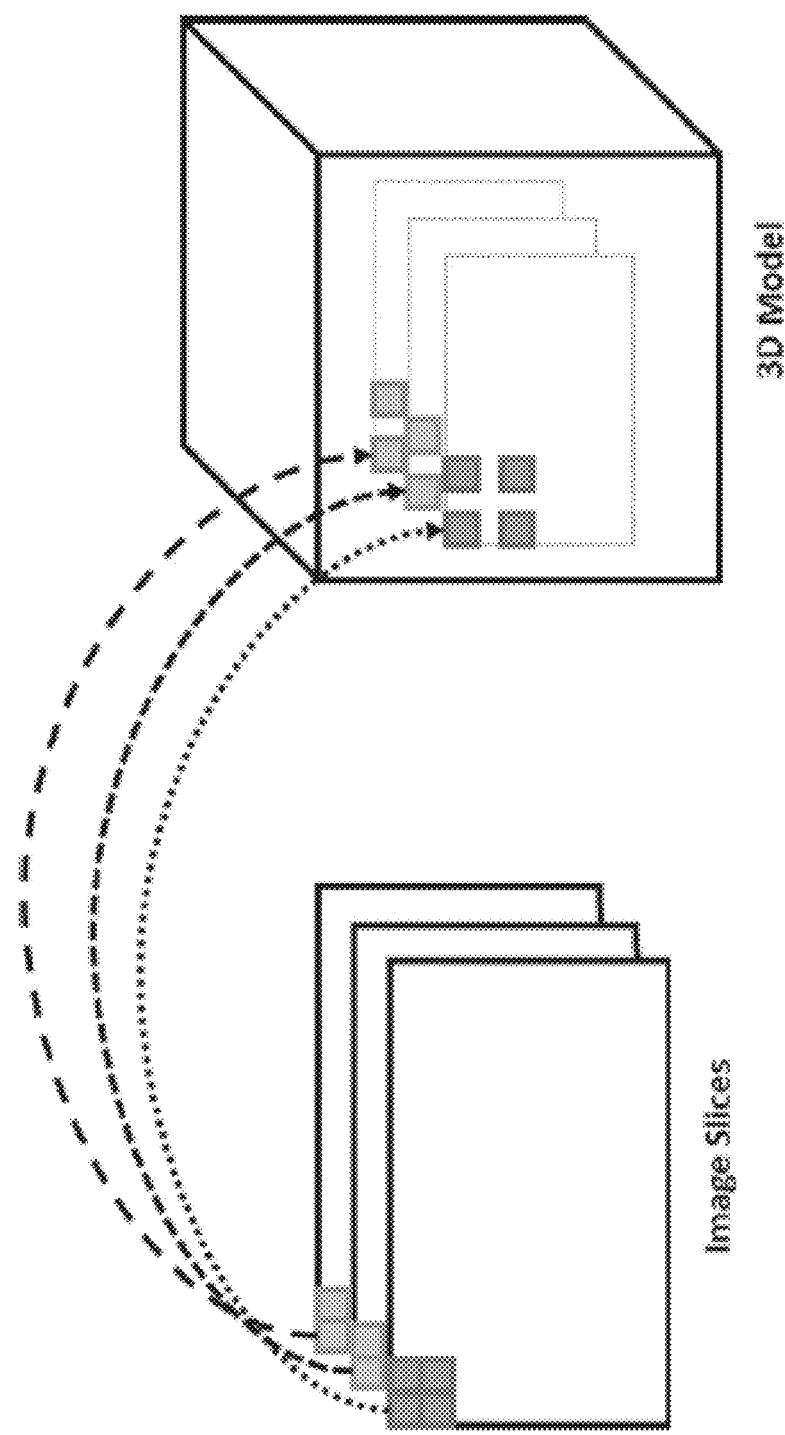
FIG. 14 is a pictorial representation of a correlation of pixels in image slices to the same pixels in a 3D model.

Fourth Stage:

Referring now to FIGS. 12-14, an embodiment of motion correction unit 308 is shown. FIG. 12 illustrates motion correction unit 308 that is configured to perform a motion correction on medical image files 102 (e.g., DICOM images). Motion correction unit 308 takes the DICOM images from scanning device 101 and the affine transformation matrices obtained from the previous stage, and generates motion-corrected image files 120. To choose the appropriate transformation matrix that has to be applied over the DICOM image, time stamps of the DICOM file and the transformation matrix are aligned. FIG. 12 shows the workflow of this stage. This stage includes three steps: a pre-motion correction step where the DICOM files and the affine matrices are aligned and a 3D volume is reconstructed from the DICOM files, the motion correction step where the affine matrices are applied over their corresponding 3D volume, and last step in which the motion corrected DICOM files are created.

Since the previous stage returns all the necessary affine matrices, this stage only requires selection and application of an appropriate transformation matrix to the DICOM images. If DICOM files have the same acquisition time, the same affine matrix can be applied to them. To make the motion correction task efficient and since the affine matrices are obtained for a 3D space, a 3D volume will be constructed from the image slices contained in the DICOM files that share the same acquisition time. This is possible because the header of the DICOM file contains the following attributes: image position, image orientation, pixel spacing in the x-axis and y-axis, slice location and slice thickness. The image position attribute gives the x, y and z coordinates of the upper left corner of the slice. The image orientation gives the direction cosines of the first row and the first column with respect to the patient. Image position and image orientation are used to properly order the slices in space. The pixel spacing attribute is the physical distance between the center of each 2D pixel in mm. It is specified by two values, where the first one is for the row spacing, $y_{spacing}$, and the second one is for the column spacing, $x_{spacing}$.

FIG. 13 shows an example to illustrate this concept where each square represents a pixel and the orange squares represents the center of the pixel. The pixel spacing attribute allows the pixels of the slice to be spaced and positioned appropriately relative to a physical distance. In addition, the slice thickness attribute represents the width in mm of the PET scanner detector used to acquire the image, and the slice location is the relative position of the image plane expressed in mm. Using the slice location attribute, the image slices can be placed in the proper location. Each pixel in the image slice generates a point in the 3D model. To generate the 3D model, for each slice, the process starts by placing the pixel in the upper left corner of the slice in 3D space. Then, it iterates through each pixel in the slice placing them in 3D space leaving the appropriate spacing, in the x and y axis, given by the pixel spacing attribute. The z coordinate of all the pixel for a specific slice is given by its slice location attribute, and the intensity of the point in 3D is given by its pixel value in the slice. FIG. 14 illustrates this concept.

Returning to FIG. 12, once the 3D volume is generated, the time stamp aligned affine matrix is applied to this volume. This process will return a motion corrected 3D model of the DICOM files for that specific acquisition time. This 3D model is used to obtain the corrected 2D images which will be returned to the scanner as a series of DICOM files. The number of 2D slices generated is equal to the number of slices given for the generation of the 3D model.

To generate the slices, the algorithm places a 2D plane perpendicular to the z-axis of the 3D model at each slice location. Then, it locates the upper left corner of the slice in the 2D plane and extracts the intensity value of that position and copies it in the corresponding pixel of the slice. To fill the rest of the pixels the algorithm "iterates" through the 2D plane, which is possible because the resolution of the output slice is the same as the resolution of the slice given to generate the 3D model and the pixel spacing is known. For example, to fill the first row of the slice, the 2D plane is sampled at every $k*x_{spacing}$, where k varies from 0 to the number of columns in the slice. Once all the pixels in the slice are obtained, the slice image is stored in the output DICOM file.

In a further embodiment, the current methodology of generating transformation matrices can be applied to the actual raw data or sinograms generated by the scanner as well as to the slices that are created from the scanner's data. In this case instead of generating unified and corrected frame files, there will be unified and corrected sonogram files. The advantage is that this will create better and faster corrections to the actual data. After the corrections have been applied to the raw data corrected slices can then be generated. In addition, in further embodiment, the current methodology also encompasses non-linear transformations that can be used to correct for motion artifacts. The use of affine transformations is for demonstration purposes and does not preclude the use of non-linear transformations. As used herein, the term "unit" may refer to, be part of, or include an Application Specific Integrated Circuit (ASIC), an electronic circuit, a processor or microprocessor (shared, dedicated, or group) and/or memory (shared, dedicated, or group) that executes one or more software or firmware programs, a combinational logic circuit, and/or other suitable components that provide the described functionality. Thus, while this disclosure includes particular examples and arrangements of the units, the scope of the present system should not be so limited since other modifications will become apparent to the skilled practitioner. Furthermore, while the above description describes hardware in the form of a processor executing code, hardware in the form of a state machine, or dedicated logic capable of producing the same effect, other structures are also contemplated.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An image motion-correction device having a processor (104) comprising instructions embedded in a non-volatile storage device, the instructions including:
    a frame file generation unit (108) configured to obtain data frames representing motion of a patient based upon motion information about the patient received from a motion tracking device;
    an image correction unit (106) configured to create affine motion matrices representing motion between the data frames;
    the image correction unit (106) configured to obtain medical image files (102) correlated in time to the data frames from a scanning device;

the image correction unit (106) configured to apply the affine motion matrices to the medical image files (102) to generate motion-corrected medical image files (120); and the image correction unit (106) configured to store the motion-corrected image files (120);

instructions to perform frame registration between consecutive frames of the data frames representing motion of the patient;

instructions to read the consecutive frames of the data frames representing motion of the patient and generate a point cloud associated with a region of interest based on the motion between the data frames and depth map data;

instructions to detect and extract at least one feature from the point cloud for generating a matched point cloud based on the detected and extracted at least one feature; and instructions to create at least one affine transformation matrix based on the matched point cloud using an optimization process.

2. The device of claim 1, wherein the frame file generation unit (108) is further configured to obtain depth map data (206) and to generate unified frame files (110) combining data frames with corresponding depth map data (206).

3. The device of claim 1, wherein the frame file generation unit (108) is further configured to obtain region of interest data (200) representing a region of interest and the image correction unit (106) is further configured to create the affine motion matrices using data in the data frames corresponding to the region of interest.

4. The device of claim 1, wherein the image correction unit (106) is further configured to create the affine motion matrices by registering pairs of data frames in parallel processes to obtain intermediate affine motion matrices representing motions between the data frames in the pairs and to register the data frames to a reference data frame using the intermediate affine motion matrices.

5. The device of claim 4, wherein the image correction unit (106) is further configured to register subsets of the data frames to different reference data frames to compensate for drift.

6. The device of claim 1, wherein the image correction unit (106) is further configured to create the affine motion matrices by extracting patient features from the data frames and matching the patient features.

7. A patient scanning system (100) comprising:
a patient scanning device (101) including sensors configured to sense signals comprising information regarding internal tissues of a patient;
a signal processor (104) to convert the sensed signals into medical image files (102);
a motion detection device (112) to capture data frames representing motion of the patient; and
an image motion-correction device as in claim 1 configured to create affine motion matrices representing motion between the data frames and generate motion-corrected medical image files (120) based on the medical image files (102) and the affine motion matrices.

8. A computing device having a processor (104) operative to:
generate at least one unified frame file (110) based on motion image data (204), depth map data (206) corresponding to the motion image data, and region of interest data (200) received from a motion tracking device;

perform frame registration between consecutive frames of the motion image data;
read the consecutive frames of the motion image data and generate a point cloud associated with the region of interest data based on the image motion data and the depth map data;
detect and extract at least one feature from the point cloud for generating a matched point cloud based on the detected and extracted at least one feature;
create at least one affine transformation matrix between the consecutive frames of the motion image data based on the matched point cloud using an optimization process;
generate at least one corrected image file (120) derived from a medical image file (102) received from a scanning device by performing the motion correction based on the at least one unified frame file (110); and
output the at least one corrected image file (120) for display to one or more display devices (122).

9. The device of claim 8, wherein the at least one processor (104) is further configured to unify the motion image data (204), the corresponding depth map data (206), and the region of interest data (200) based on a time stamp for generating the at least one unified frame file (110).

10. The device of claim 8, wherein the at least one processor (104) is further configured to perform model registration for all frames of the motion image data (204) with respect to a reference frame using the at least one affine transformation matrix.

11. The device of claim 8, wherein the at least one processor (104) is further configured to perform the motion correction on the medical image file (102) based on the at least one affine transformation matrix.

12. The device of claim 11, wherein the at least one processor (104) is further configured to align chronologically the medical image file (102) and the at least one affine transformation matrix to select which affine transformation matrix is applied against the medical image file (102).

13. The device of claim 12, wherein the at least one processor (104) is further configured to generate a three-dimensional volume of the medical image file (102) based on the selected affine transformation matrix.

14. The device of claim 13, wherein the at least one processor (104) is further configured to generate the at least one corrected image file (120) based on the three-dimensional volume of the medical image file (102).

15. A patient scanning system (100) comprising:
a patient scanning device (101) including sensors configured to sense signals comprising information regarding internal tissues of a patient;
a motion detection device (112) to capture data frames representing motion of the patient;
a motion determination device configured to create affine motion matrices representing motion between the data frames; and
a signal processor (104) to convert the sensed signals into motion-corrected medical image files (120) using the affine motion matrices; and
wherein the patient scanning system:
performs frame registration between consecutive data frames;
reads the consecutive data frames and generates a point cloud associated with region of interest data based on the motion between the data frames and depth map data;

detects and extracts at least one feature from the point cloud for generating a matched point cloud based on the detected and extracted at least one feature; and
creates at least one affine transformation matrix between the consecutive data frames based on the matched point cloud using an optimization process.

* * * * *